US011419798B2

(12) United States Patent
Seo et al.

(10) Patent No.: US 11,419,798 B2
(45) Date of Patent: Aug. 23, 2022

(54) DEVICE FOR PRODUCING SKIN CARE PACK USING HYDROGEL, AND CONTROL METHOD THEREOF

(71) Applicant: Amorepacific Corporation, Seoul (KR)

(72) Inventors: Jeong Eun Seo, Yongin-si (KR); Ji Hoon Kim, Yongin-si (KR); Sung Won Yi, Yongin-si (KR); Seung Hoon Park, Incheon (KR); Keun Sik Choi, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 344 days.

(21) Appl. No.: 16/650,684

(22) PCT Filed: Sep. 27, 2018

(86) PCT No.: PCT/KR2018/011469
§ 371 (c)(1),
(2) Date: Mar. 25, 2020

(87) PCT Pub. No.: WO2019/059747
PCT Pub. Date: Mar. 28, 2019

(65) Prior Publication Data
US 2020/0222289 A1 Jul. 16, 2020

(30) Foreign Application Priority Data
Sep. 25, 2017 (KR) .................. 10-2017-0123807

(51) Int. Cl.
*A61K 8/02* (2006.01)
*A61K 8/04* (2006.01)
(Continued)

(52) U.S. Cl.
CPC ............ *A61K 8/042* (2013.01); *A45D 44/002* (2013.01); *A45D 44/22* (2013.01); *A61K 8/0212* (2013.01);
(Continued)

(58) Field of Classification Search
CPC .... A61K 8/042; A61K 8/0212; A45D 44/002; A45D 44/22; A45D 2200/1036;
(Continued)

(56) References Cited

U.S. PATENT DOCUMENTS 5,785,960 A * 7/1998 Rigg .................... A61B 5/0059
700/239
11,172,750 B2 * 11/2021 Park .................... B01F 33/8442
(Continued)

FOREIGN PATENT DOCUMENTS

EP          3205328 A1 *  8/2017 ........... A45D 44/002
KR   10-2014-0019656 A    2/2014
(Continued)

OTHER PUBLICATIONS

International Search Report for PCT/KR2018/011469 dated Jan. 7, 2019 (PCT/ISA/210).
(Continued)

*Primary Examiner* — Nicolas A Arnett
(74) *Attorney, Agent, or Firm* — Sughrue Mion, PLLC

(57) ABSTRACT

A device for producing a skin care pack using a hydrogel and a control method thereof are disclosed. The device may include a housing which is provided with a door for selectively opening and closing a work space for forming a skin care pack, and which maintains a forming temperature required for producing the skin care pack; a platform including a base supported on a floor plate of the work space, and a heater for heating hydrogel discharged onto the base; a former including nozzle modules which are provided to be
(Continued)

movable in the work space and each include a pump for receiving and discharging a heated hydrogel; and a control unit which controls the movement of the nozzle modules and the operation of the pumps, and maintains the temperature of the base to a predetermined range by controlling the operation of the heater.

19 Claims, 13 Drawing Sheets

(51) Int. Cl.
  *A45D 44/00*    (2006.01)
  *A45D 44/22*    (2006.01)
  *B29C 64/106*    (2017.01)
  *B29C 64/209*    (2017.01)
  *B29C 64/00*    (2017.01)
  *B29B 11/00*    (2006.01)
  *B32B 37/00*    (2006.01)
  *B65B 3/00*    (2006.01)
  *B65B 3/04*    (2006.01)
  *B65B 3/12*    (2006.01)
  *B65B 63/08*    (2006.01)
  *A61Q 19/00*    (2006.01)

(52) U.S. Cl.
  CPC ............. *B29B 11/00* (2013.01); *B29C 64/00* (2017.08); *B29C 64/106* (2017.08); *B29C 64/209* (2017.08); *B32B 37/00* (2013.01); *B65B 3/00* (2013.01); *B65B 3/04* (2013.01); *B65B 3/12* (2013.01); *B65B 63/08* (2013.01); *A45D 2200/1036* (2013.01); *A61Q 19/00* (2013.01); *B65H 2701/1752* (2013.01)

(58) Field of Classification Search
  CPC ......... A61Q 19/00; B29B 11/00; B29C 64/00; B29C 64/106; B29C 64/209; B32B 37/00; B65B 3/00; B65B 3/04; B65B 3/12; B65B 63/08; B65H 2701/1752
See application file for complete search history.

(56) References Cited

U.S. PATENT DOCUMENTS

| | | | | |
|---|---|---|---|---|
| 2010/0191314 | A1* | 7/2010 | Young | A45D 44/002 607/109 |
| 2011/0056943 | A1* | 3/2011 | Ueda | A61K 8/676 53/484 |
| 2011/0180449 | A1* | 7/2011 | Rubin | A61K 8/11 424/70.13 |
| 2014/0120144 | A1* | 5/2014 | Abe | A61Q 19/08 156/60 |
| 2017/0231876 | A1* | 8/2017 | Park | A61Q 19/00 424/401 |
| 2017/0340090 | A1* | 11/2017 | Kim | A61K 8/466 |
| 2019/0350344 | A1* | 11/2019 | Park | A45D 44/002 |
| 2020/0238600 | A1* | 7/2020 | Seo | B33Y 10/00 |
| 2020/0238622 | A1* | 7/2020 | Seo | B29C 64/393 |
| 2020/0316858 | A1* | 10/2020 | Seo | B29C 64/106 |
| 2020/0317542 | A1* | 10/2020 | Dijkstra | C02F 1/4618 |

FOREIGN PATENT DOCUMENTS

| | | | | |
|---|---|---|---|---|
| KR | 10-1556078 B1 | 9/2015 | | |
| KR | 10-1561476 B1 | 10/2015 | | |
| KR | 10-1668310 B1 | 10/2016 | | |
| KR | 10-2016-0126628 A | 11/2016 | | |
| KR | 2040403 B1 * | 11/2019 | | A45D 34/04 |

OTHER PUBLICATIONS

Written Opinion of the International Searching Authority for PCT/KR2018/011469 dated Jan. 7, 2019 (PCT/ISA/237).

* cited by examiner

[FIG. 1]
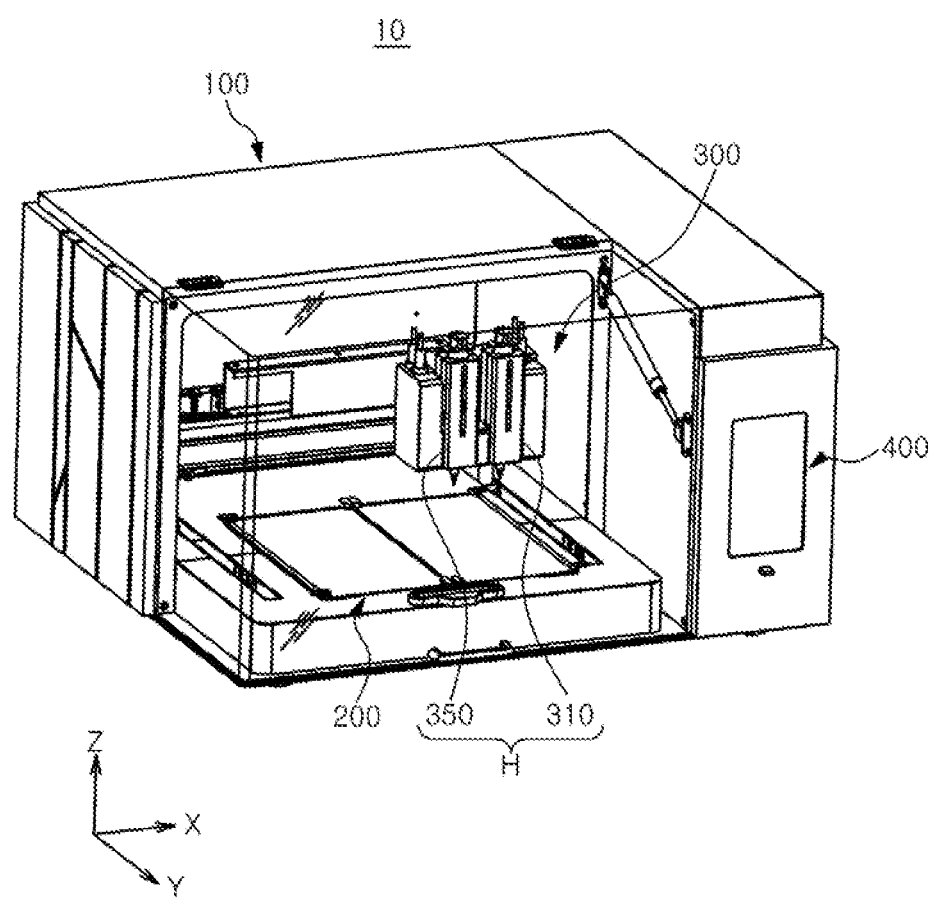

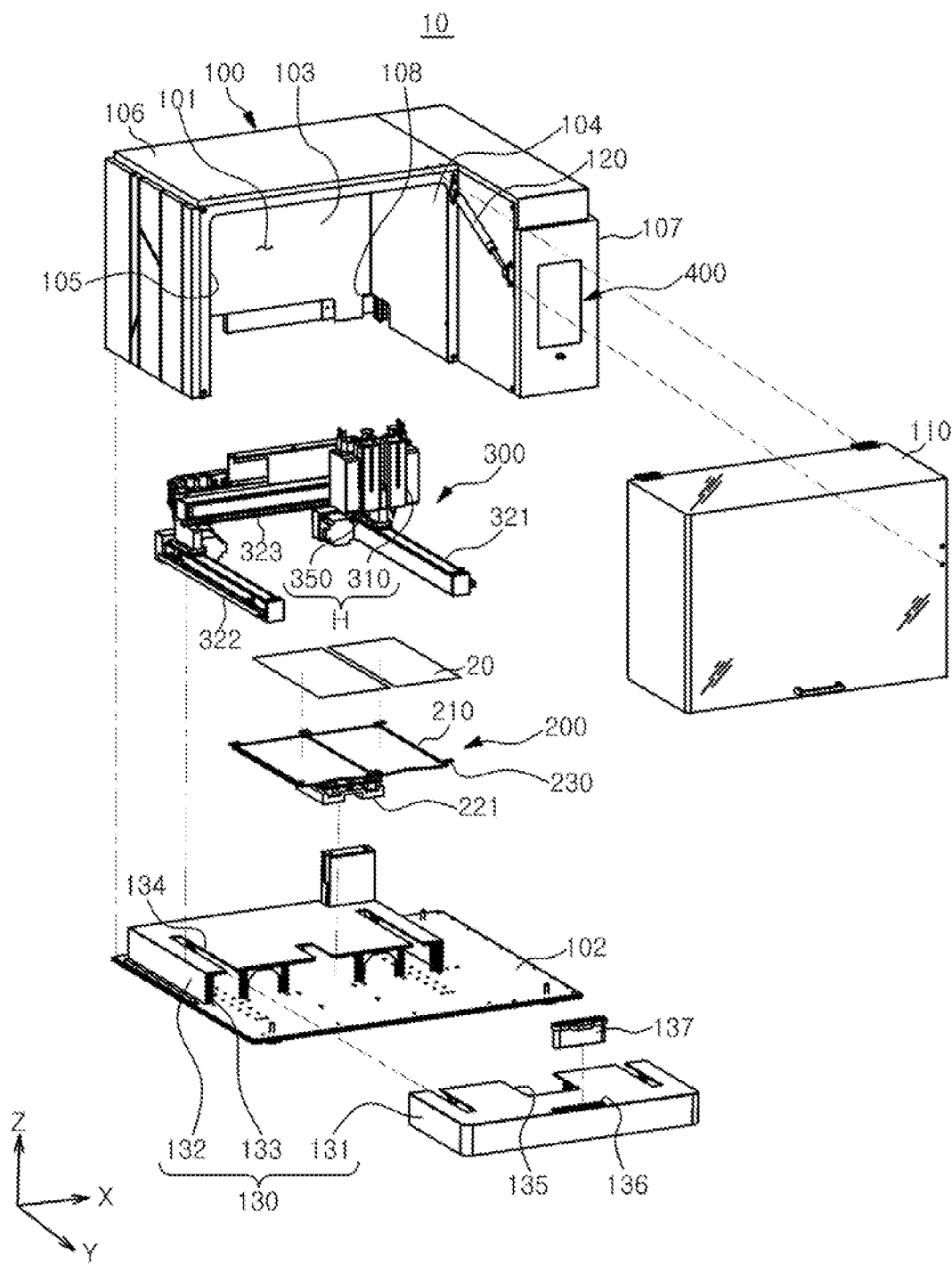
[FIG. 2]

[FIG. 3]
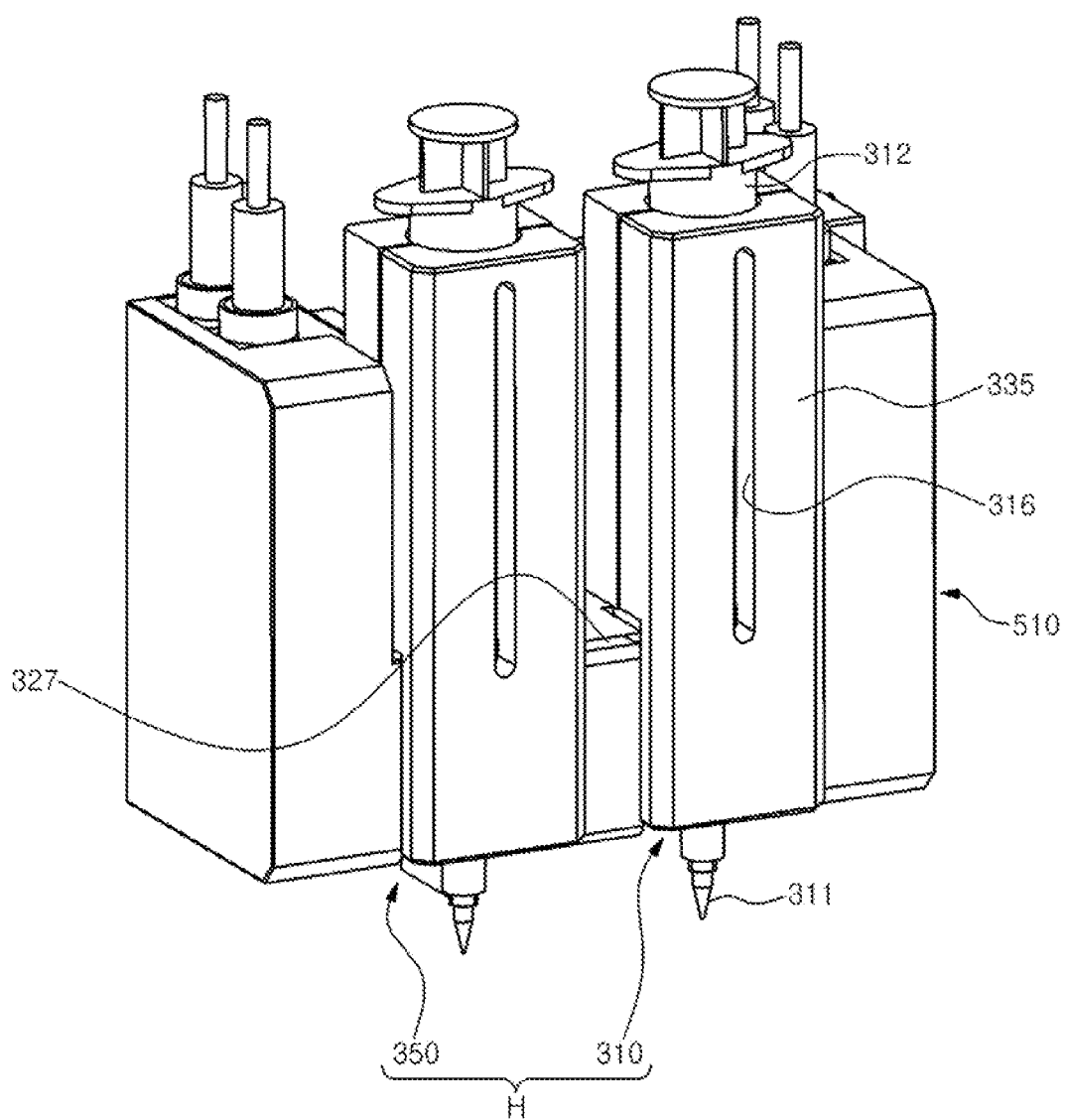

[FIG. 4]
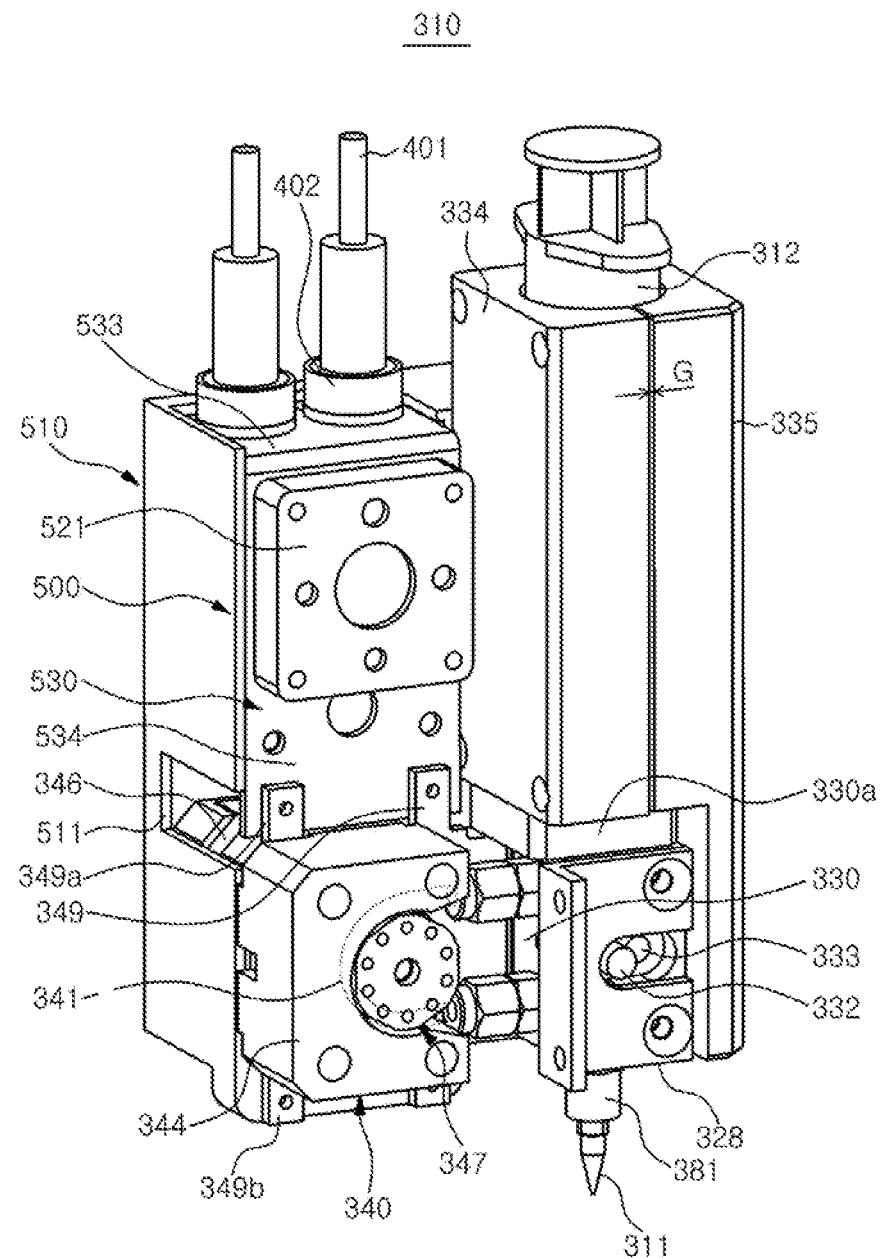

[FIG. 5]
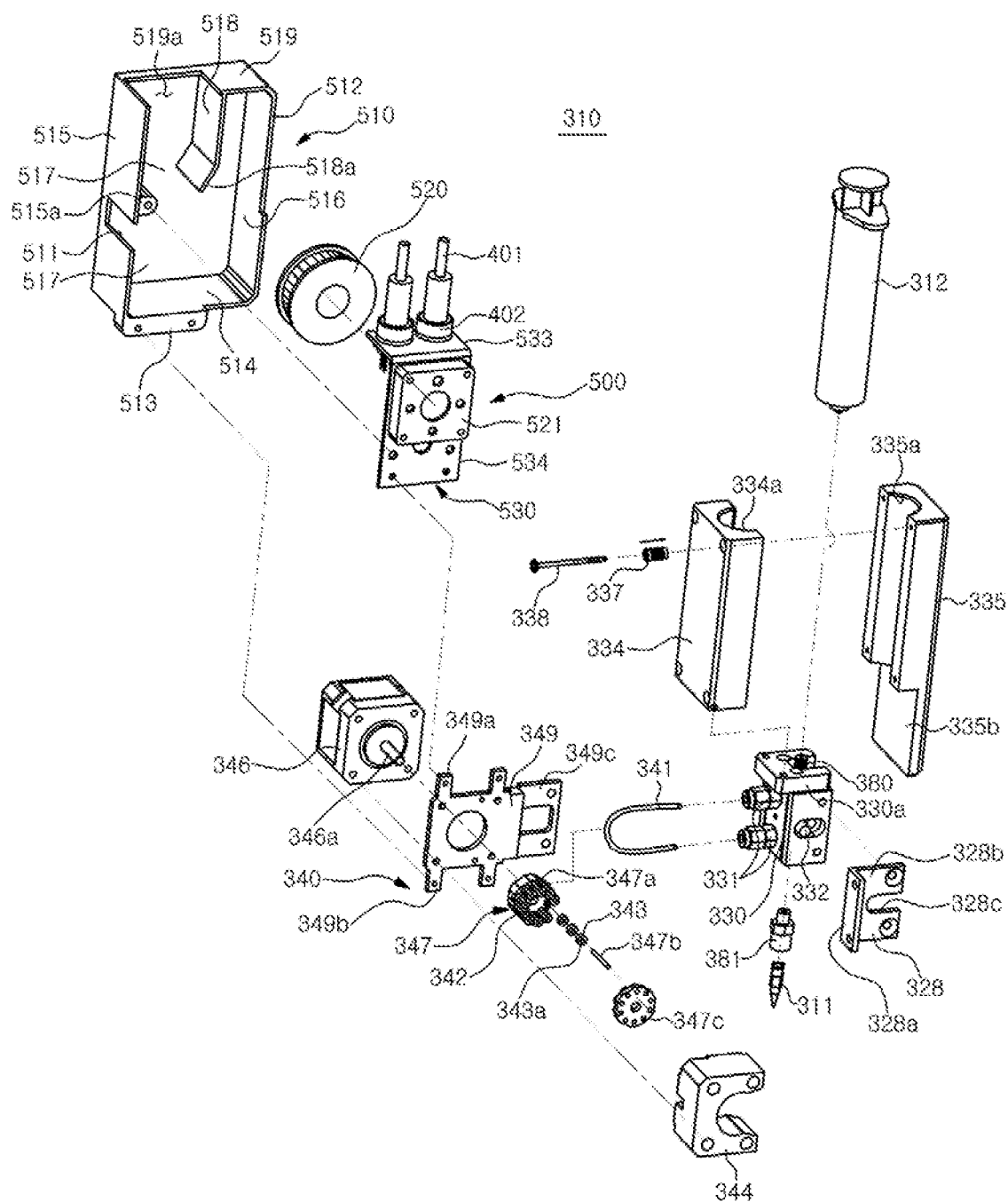

[FIG. 6]
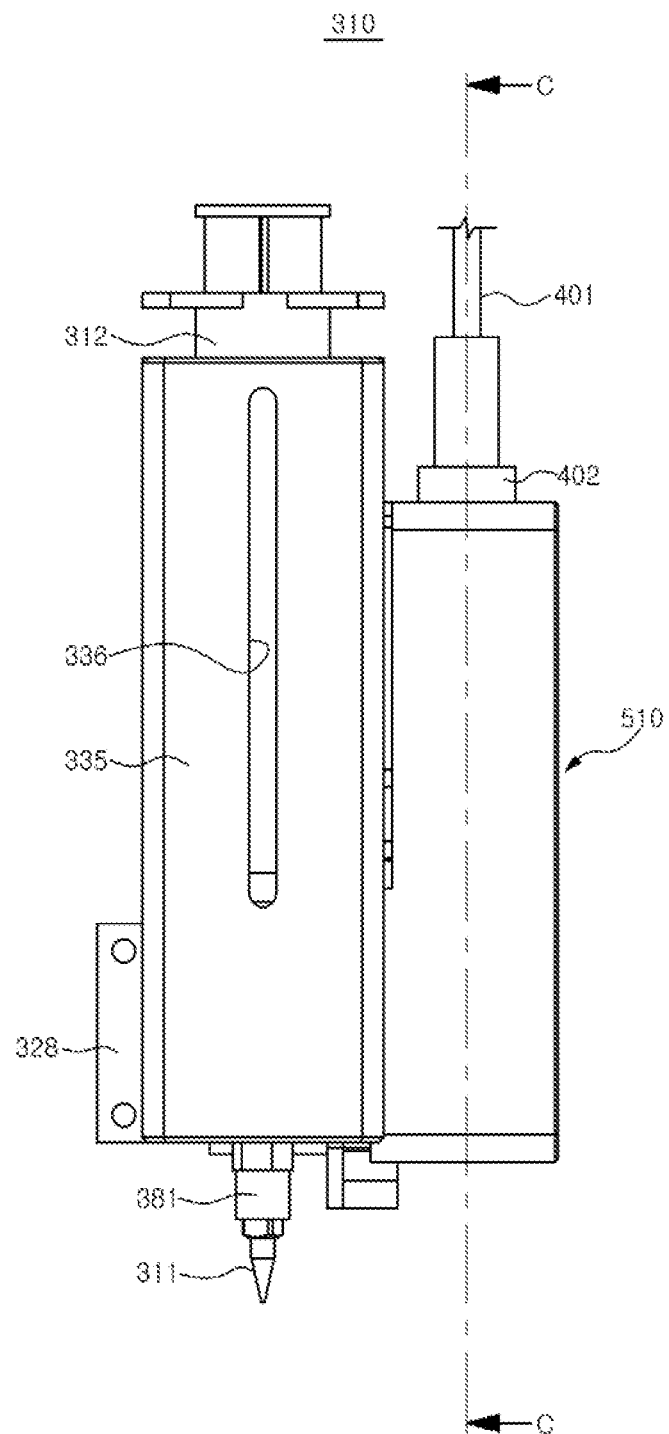

【FIG. 7】
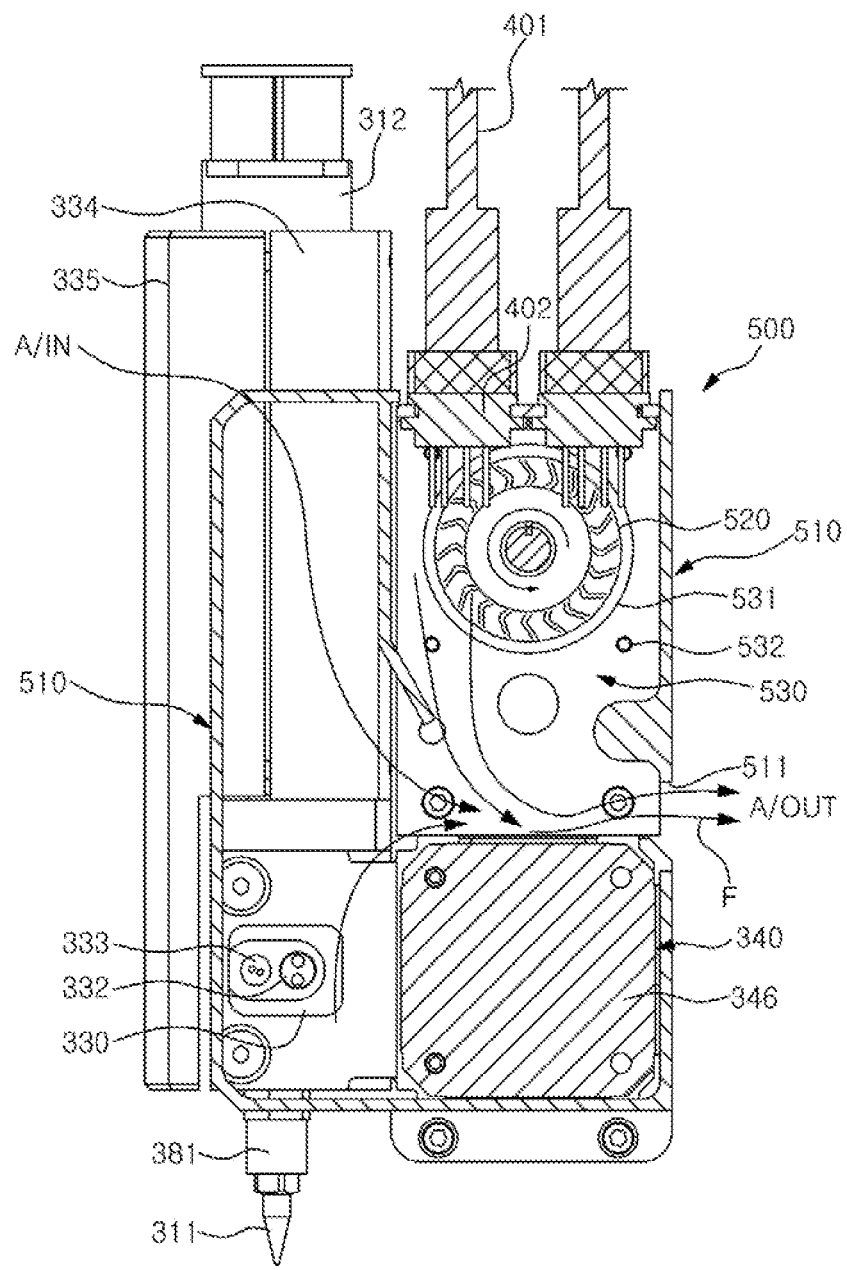

[FIG. 8]
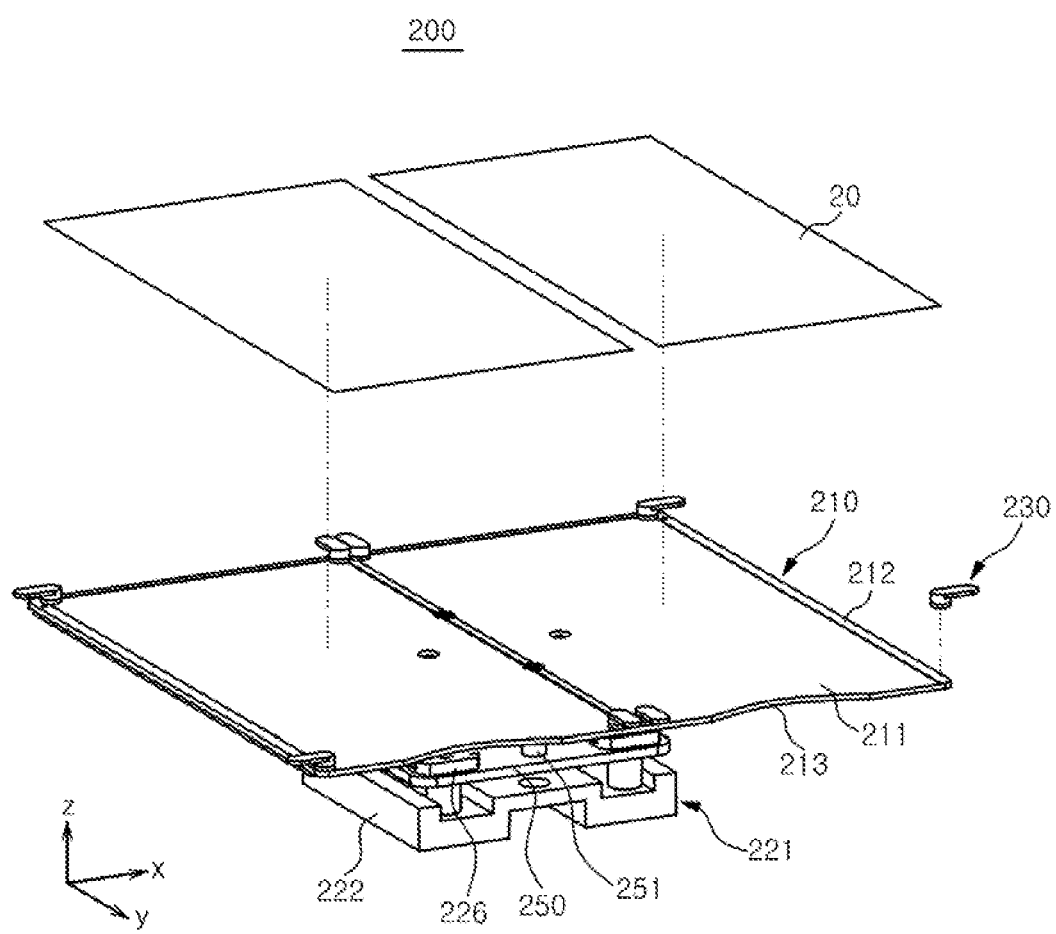

[FIG. 9]
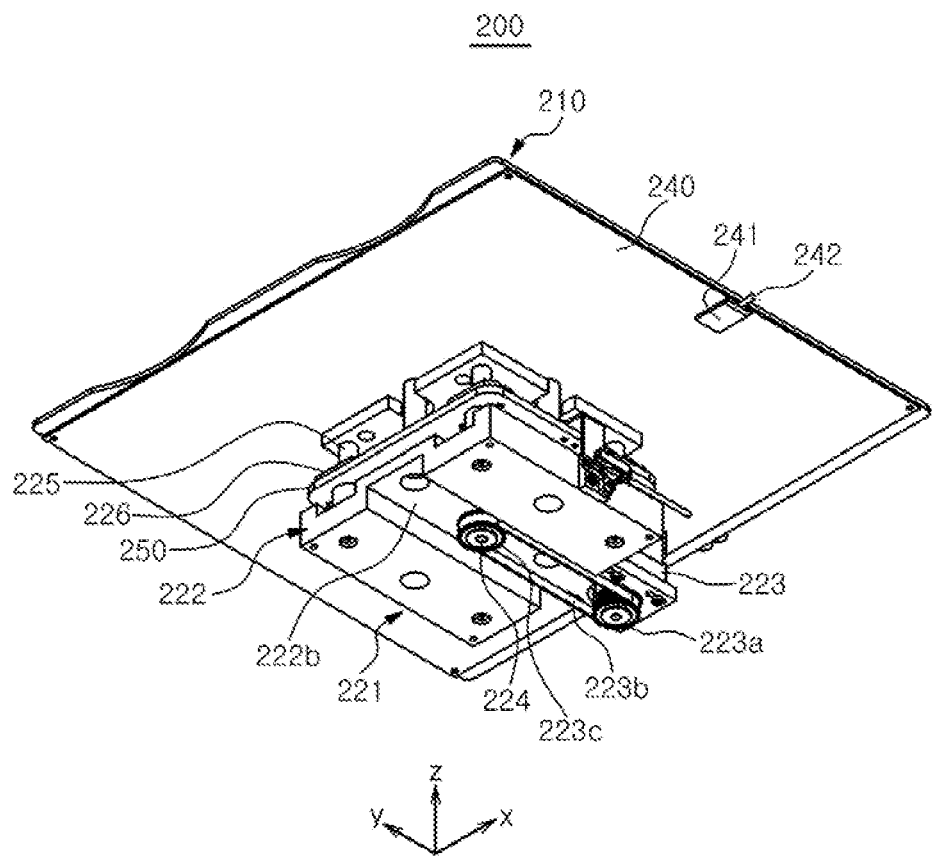

[FIG. 10]
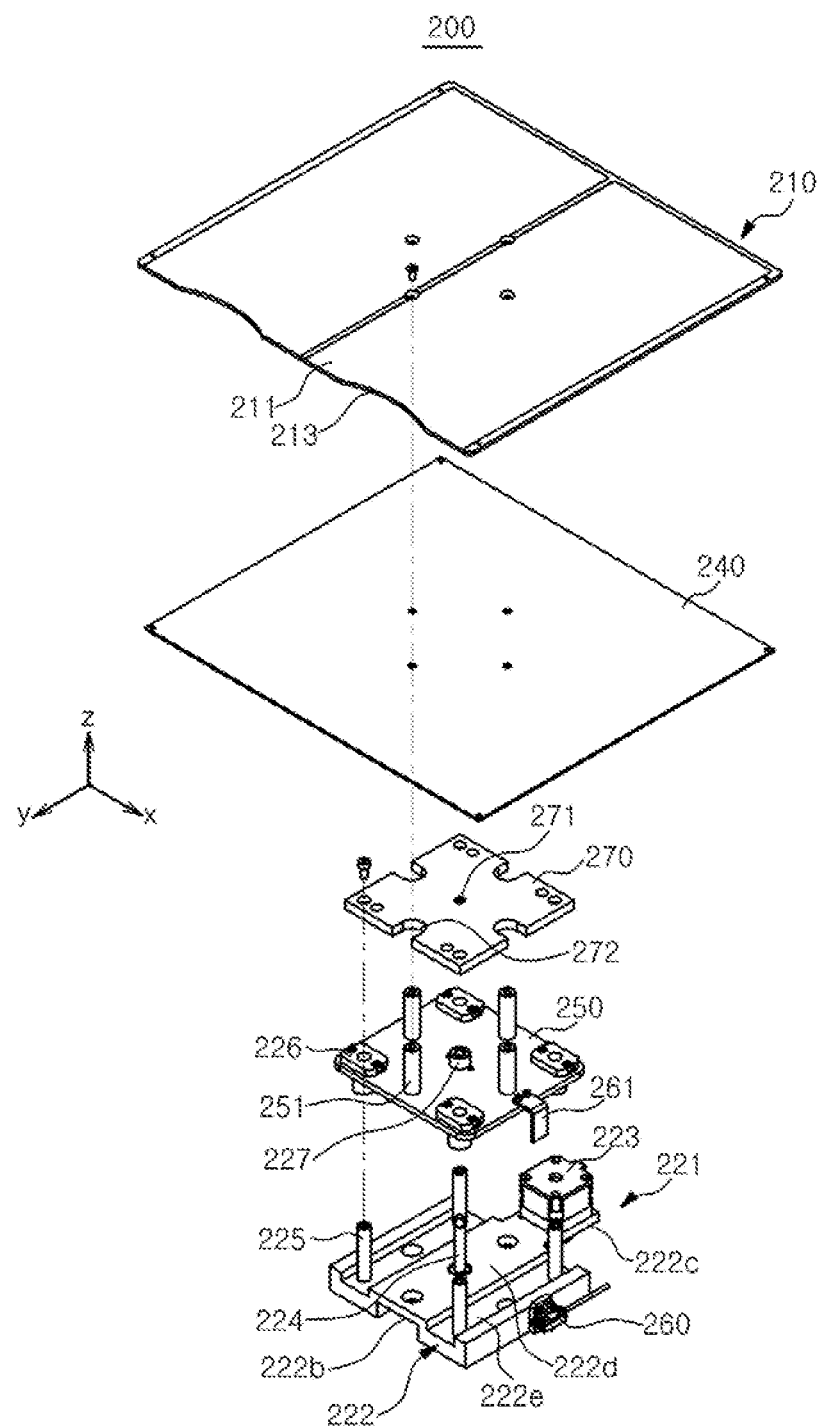

[FIG. 11]
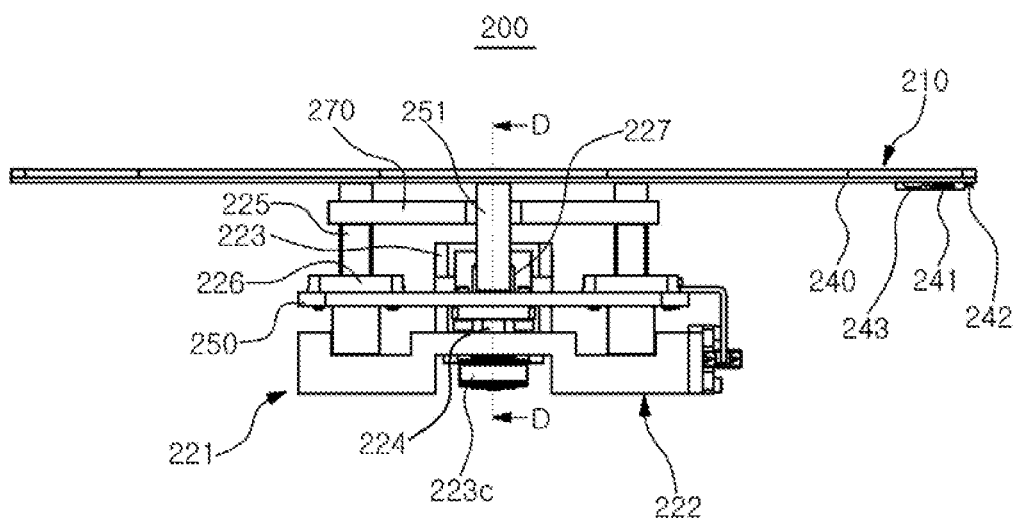

[FIG. 12]
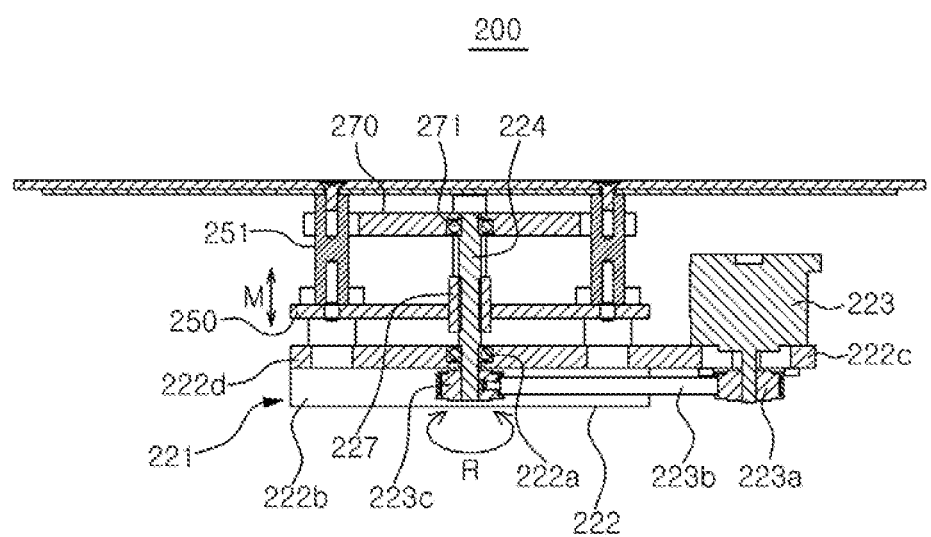

[FIG. 13]
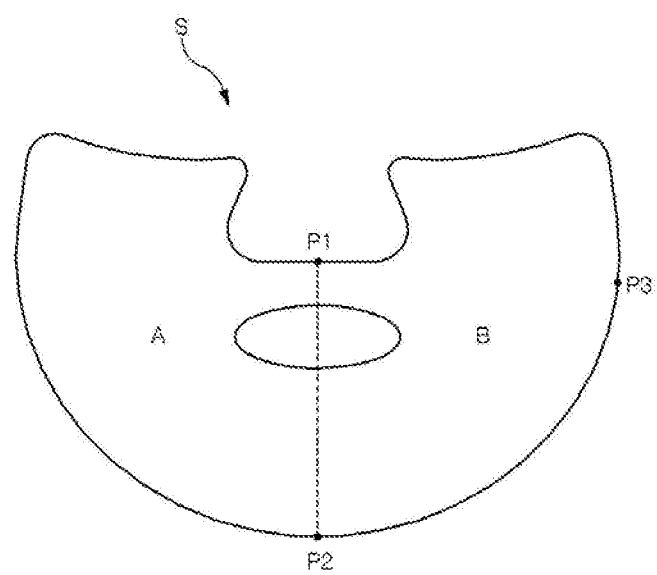

DEVICE FOR PRODUCING SKIN CARE PACK USING HYDROGEL, AND CONTROL METHOD THEREOF

CROSS REFERENCE TO RELATED APPLICATIONS

This application is a National Stage of International Application No. PCT/KR2018/011469 filed Sep. 27, 2018, claiming priority based on Korean Patent Application No. 2017-1023807, filed Sep. 25, 2017, with the Korean Intellectual Property Office, the entire contents of which are hereby incorporated by reference.

TECHNICAL FIELD

The present invention relates to a device for producing a skin care pack using hydrogel, and a control method thereof.

BACKGROUND ART

In general, a mask pack is a kind of cosmetic which can relatively conveniently and effectively perform skin care such as skin winkle, skin elasticity, gloss or the like by supplying moisture and nutrition to skin.

Such mask pack may be tailored in view of a face contour and positions of eyes, a nose and a mouth on a face model basis for each year group of usual users. In addition, in the case of a three-dimensional mask pack, it may be constituted by a plurality of sheet parts so that it can closely contact each part of a face, such as a forehead, both chicks, nose, chin and the like.

The mask packs have various forms such as a sheet product of non-woven fabric material to which a liquid such as a skin lotion is applied, a mask pack product which improves wearing-feeling by having an essence contained within a fabric, such as cotton, a mask pack product which uses hydrogel, or a bio-cellulose mask pack product which uses a natural material. As the mask pack product using the hydrogel among these has an advantage that a functional component for skin care is selectively contained or mixed, demand for a hydrogel mask pack is increasing.

Meanwhile, a manufacturer mass-produces and supplies mask packs to the market using a factory automation system which can produce a great number of mask packs for a short time period after determining a product standard based on a face model of a universal user for mass production.

The mask packs supplied by mass-production are getting good response in the market because they exhibit their effects beyond a certain level at a relatively inexpensive price. But a user cannot use a mask pack which perfectly fits to his/her own skin due to the limit of mass production system. So, there is a drawback that a user cannot feel enough satisfaction with it.

Under this background, recently there have been trials to produce a custom-tailored mask pack. Specifically, there is suggested a technology which generates a 3D model of a user face, and produces a mask pack fit to a face shape of a user using it. This prior art is characterized by fabricating a base such as non-woven fabric or cotton based on modeled data so as to fit to a user's face, or applying substance for skin care to a specific region of the base in view of a face shape of a user.

However, a device for producing the above-described customized mask pack or a producing method is applicable to a mask pack having a base, but none of them can be applied to producing a hydrogel mask pack for which demand is increasing recently. That is because hydrogel is in a semi-solid state at a room temperature and thus is required to be heated for forming, which may lead to a drawback that, when the hydrogel is heated, its viscosity is decreased and the hydrogel leaks from a nozzle through which the hydrogel is discharged. That is, with the prior manner, it is very difficult or substantially impossible to precisely control a discharge timing, a discharge position and a discharge amount of the hydrogel in order to produce a customized mask pack.

Further, if the heating temperature of the hydrogel is lowered in order to prevent this problem, its viscosity enough for forming cannot be acquired, and thus there is no way except that productivity of a mask pack is extremely lowered or quality of the final product becomes very bad.

With regard to this, Korean patent application publication No. 10-2017-0070699 (Published on Jun. 22, 2017) provides "Manufacturing method of 3D-hydrpogel mask", and however, it is only intended to optimize the hydrogel contents, while still having the above-described problem. Thus, it cannot become a substantial countermeasure for producing the hydrogel mask pack.

Meanwhile, nowadays, as the interest in skin care increases, skin care products for each part of a physical body such as a hand, an arm, a foot, a leg or the like are being launched, and however, such skin care products also have the above-described problem. Therefore, there is an increasing need for a customized product and a product for which a raw material is the hydrogel.

DISCLOSURE

Technical Problem

Embodiments of the invention provide a device for producing a skin care pack for which a raw material is hydrogel, and a control method thereof.

Additionally, embodiments of the invention provide a manufacturing device for producing a skin care pack rapidly and precisely in spite of using hydrogel as a raw material, and a control method thereof.

Further, embodiments of the invention provide a manufacturing device for producing a high quality hydrogel skin care pack and a control method thereof.

Also, embodiments of the invention provide a device for producing a skin care pack using hydrogel, which is optimized for body characteristics of a user, and a control method thereof.

Technical Solution

According to an aspect of the present invention, there is provided a device for producing a skin care pack using hydrogel, the device comprising: a housing which is provided with a door for selectively opening and closing a work space for forming a skin care pack and which maintains a forming temperature required for producing the skin care pack; a platform including a base supported on a floor plate of the work space of the housing and a heater for heating hydrogel discharged onto the base; a former including one or more nozzle modules which are provided to be movable in the work space, each nozzle module having a pump for receiving a heated hydrogel and then discharging the same onto the platform through a nozzle; and a control unit which controls the movement of the nozzle modules and the operation of the pumps, and maintains the temperature of the base to a predetermined range by controlling the operation of the heater.

Further, there is provided a device for producing a skin care pack using hydrogel, wherein the heater is a pad type or film type heating element which is installed on a lower part of the base.

Further, there is provided a device for producing a skin care pack using hydrogel, wherein the heater has a planar area corresponding to a lower surface of the base.

Further, there is provided a device for producing a skin care pack using hydrogel, wherein on the base, a film is seated to which hydrogel is discharged to form a skin care pack, the base is formed of a thermally conductive material, so that it can transfer heat through the film to a skin care pack which is formed, and the heater heats the base.

Further, there is provided a device for producing a skin care pack using hydrogel, wherein on the platform, there is provided a temperature sensor which measures temperature of the base or the heater, and the control unit controls the heater based on a value which has been measured by the temperature sensor.

Further, there is provided a device for producing a skin care pack using hydrogel, wherein the skin care pack is produced in one or more divided segments, one of the segments has a plurality of portions connected to each other, each portion being continuously formed, and when one of the portions is formed to be discontinuous with another portion, the one portion and the other portions are connected to each other after a predetermined period of time has elapsed.

Further, there is provided a device for producing a skin care pack using hydrogel, wherein the nozzle module further includes a cooling device which cools down a pump motor of the pump, and wherein the cooling device includes a cooling fan disposed on a side of the pump motor, cools down the pump motor with flow generated at the cooling fan, and discharges to the work space the flow which has absorbed heat from the pump motor.

Further, there is provided a device for producing a skin care pack using hydrogel, wherein the former moves the nozzle module in an x-axis and y-axis directions, and the platform includes a z-axis linear driving device which moves the base in a z-axis direction.

Further, there is provided a device for producing a skin care pack using hydrogel, wherein the z-axis linear driving device includes: a bottom block installed at a floor plate of the housing; a driving motor disposed at a side of the bottom block; a ball screw shaft to which a rotational force of the driving motor is transferred, and which is rotatably combined based on the bottom block; a plurality of guide bars which are dispersedly disposed at a plurality of points of the bottom block based on the ball screw shaft; and guide blocks which are slidably combined to the guide bars respectively.

Further, there is provided a device for producing a skin care pack using hydrogel, wherein the z-axis linear driving device includes: a ball screw block which is combined to the ball screw shaft, and which converts a rotational force of the ball screw shaft to a conveying force; and a movable frame which the ball screw block is installed at a central position thereof, and wherein the guide blocks are installed at frame corner positions of the movable frame respectively.

Further, there is provided a device for producing a skin care pack using hydrogel, wherein the bottom block includes: a first sub-block at which the driving motor is installed; a second sub-block which integrally extends from the first sub-block and which is provided with a disposition space of a driving force transmission mechanism; and a third sub-block which are integrally formed on both sides of the second sub-block and which is provide with a groove.

Further, there is provided a device for producing a skin care pack using hydrogel, wherein the driving force transmission mechanism includes: a driving pulley axially combined to a shaft of the driving motor; a driven pulley axially combined to the ball screw shaft; and a belt interconnecting the driving pulley and the driven pulley.

Further, there is provided a device for producing a skin care pack using hydrogel, wherein the z-axis linear driving device includes: a sensor bar which extends toward the bottom block from a side of the movable frame; and a displacement sensor provided at a side surface of the bottom block so as to sense change in a magnetic field by the sensor bar.

Further, there is provided a device for producing a skin care pack using hydrogel, wherein the z-axis linear driving device includes: a plurality of support bars which are supported by the movable frame with reference to positions which are not superimposed on the guide blocks, each support bar is installed at the upper surface of the movable frame corresponding to a position between the guide bars, and wherein the base is combined to the end of the support bar so as to be supported by the support bar.

Further, there is provided a device for producing a skin care pack using hydrogel, wherein the z-axis linear driving device includes: a fixed frame which is disposed between the movable frame and the heater, and which is combined to the end of the guide bar.

Further, there is provided a device for producing a skin care pack using hydrogel, wherein the fixed frame includes a bearing arranged in a central position of the fixed frame and coupled with the end portion of a ball screw shaft; and a recess formed in a side of the fixed frame for passing the support bar, wherein the platform support the movable frame and the base by connecting by the plurality of guide bars the fixed frame and the bottom block which are disposed spaced apart from each other along a vertical direction of the platform and parallel to each other to form a frame type structure.

According to another aspect of the present invention, there is provided a control method of a device for producing a skin care pack using hydrogel which forms the skin care pack, in which a control unit controls a relative movement of a platform on which the skin care pack is formed and a former which discharges heated hydrogel, and hydrogel is discharged toward the platform through at least one nozzle module provided in the former, wherein the nozzle module includes a peristaltic pump, the control method comprising: controlling a temperature of the main block or a temperature of the hydrogel moving through the main block within a temperature range corresponding to a heating condition of a mask pack forming; controlling a relative movement of the platform and the former; discharging heated hydrogel at a nozzle of the nozzle module by activating the peristaltic pump; maintaining a temperature of a base to which hydrogel is discharged to a predetermined range with a heater provided to the platform; and returning the former to its initial position of operation by causing relative movement between the platform and the former after a pattern part of a skin care pack has been completed.

Further, there is provided a control method of a device for producing a skin care pack using hydrogel, wherein the temperature of the base is lower than that of hydrogel which is discharged at the nozzle module.

Further, there is provided a control method of a device for producing a skin care pack using hydrogel, further comprising: cooling a motor of the peristaltic pump by activating a cooling device provided at a side of the main block, wherein flow which has cooled down the motor of the peristaltic pump is discharged to a work space in which a skin care pack is formed.

Further, there is provided a control method of a device for producing a skin care pack using hydrogel, wherein the platform includes a z-axis linear driving device, and wherein the controlling of the relative movement includes: moving the base in a z-axis direction.

Advantageous Effects

According to a device for producing a skin care pack using hydrogel and a control method thereof according to the embodiments of the present invention, there is an effect of being capable of producing a skin care pack for which a raw material is the hydrogel.

Further, there is an advantage of producing a skin care pack rapidly and precisely even though using hydrogel as a raw material.

In addition, there is an advantage of being capable of producing a high quality a hydrogel skin care pack.

Further, there is an advantage of being capable of producing

DESCRIPTION OF DRAWINGS

FIG. 1 is a perspective view of a device for producing a skin care pack using hydrogel according to an embodiment of the invention.

FIG. 2 is an exploded perspective view of the device for producing a skin care pack using hydrogel shown in FIG. 1.

FIG. 3 is an enlarged perspective view of the discharge unit shown in FIG. 2.

FIG. 4 is a perspective view of a nozzle module in a discharge unit shown in FIG. 3.

FIG. 5 is an exploded perspective view of the nozzle module shown in FIG. 4.

FIG. 6 is a front view of the nozzle module shown in FIG. 4.

FIG. 7 is a cross-sectional view taken along a line C-C shown in FIG. 6.

FIG. 8 is an enlarged perspective view of the platform shown in FIG. 2.

FIG. 9 is a perspective view showing a lower surface of the platform shown in FIG. 8.

FIG. 10 is an exploded perspective view of the platform shown in FIG. 8.

FIG. 11 is a front view of the platform shown in FIG. 8.

FIG. 12 is a cross-sectional view taken along a line D-D shown in FIG. 11.

FIG. 13 is a plan view of a segment produced by the device shown in FIG. 1.

BEST MODE

Hereinafter, specific exemplary embodiments of the invention will be described in detail with reference to the drawings.

Additionally, it is noted that in the description of the invention, the detailed description for known related configurations or functions may be omitted when it is deemed that such description may obscure essential points of the invention.

FIG. 1 is a perspective view of a device for producing a skin care pack using hydrogel according to an embodiment of the invention; and FIG. 2 is an exploded perspective view of the device for producing a skin care pack using hydrogel shown in FIG. 1; and FIG. 3 is an exploded perspective view of the former shown in FIG. 2.

Referring to FIGS. 1 to 3, a device 10 for producing a skin care pack using hydrogel according to an embodiment of the invention includes a housing 100, a platform 200, a former 300 and a control unit 400.

In the embodiment, as a device that is intended to produce a skin care pack for which a raw material is hydrogel and which may be attached to the skin for use by a user, a device 10 for producing a skin care pack using the hydrogel may produce a skin care pack based on modeling data for any body part such as a face, a hand, an arm, a foot, a leg or the like of the user. In the embodiment and the description blow, the skin care pack using the hydrogel is described by way of example as being a mask pack which is for attachment to a user's face, but the technical idea of the invention is not limited to this.

The housing 100 may be provided with a work space 101 which becomes a movement space of a discharge unit H for forming a mask pack, and a door 110 which selectively opens and closes the work space 101. The housing 100 may be configured to maintain a forming temperature required for producing a mask pack in a state where the door 110 is closed.

The platform 200 has a base 210 which is supported on a floor plate 102 of the work space 101 of the housing 100, and whose movement in a vertical direction is controlled. Here, the base 210 may be formed with a thermally conductive material, and transfer heat through the film 20 to a skin care pack which is being formed.

Further, the platform 200 may adjust displacement of the base 210 of the platform 200 (e.g., height) correspondingly to the relative movement to the former 300.

The former 300 may be disposed in the work space 101 of the housing 100 with respect to an upper position of the platform 200. The former 300 may discharge onto the platform 200 a raw material for forming a mask pack. For example, the former 300 functions to form a mask pack on the film 20 by discharging a raw material onto the film 20 which is supportable by or separable from the base 210 of the platform 200. Here, the raw material may be in a heating condition state, for example, in a state where it is heated to a level of about 90° C., within the nozzle modules 310, 350 of the discharge unit H. The heating condition may be set by the control unit 400 and controlled through a temperature sensor. For the purpose of this, a heater and a temperature sensor may be mounted on the former 300 as described below.

In the embodiment, a raw material or a mixed raw material which is capable of being stored in a cartridge (not shown) or a syringe and discharged by pumping in order to form a custom-tailored mask pack, and the raw material may be one which has properties as a semisolid substance or gel at room temperature, but which, when it is heated, has properties as a liquid while its viscosity decreases below a certain level.

For example, the raw material may be any one of hydrogel, gel type synthetic resin and a material which contains a raw material for a functional cosmetic in polymer, and in the embodiment, it is described by way of example as being the hydrogel.

The control unit 400 may include an input/output display device (e.g., a touch screen), an electronic circuit device and a power supply connected thereto.

The control unit 400 may control operation of the former 300 and the platform 200, receive the input of setpoints required for forming a mask pack and custom-tailored model CAD data, and display an operation state. In addition, the control unit 400 may be disposed on a side portion of the housing 100. That is, the control unit 400 may control the relative movement between the platform 200 and the former 300.

In this regard, the control unit 400 may calculate or set a movement path of the former 300, a discharge speed, a discharge amount, a discharge timing of hydrogel or the like for forming a mask pack. That is, the control unit 400 controls the discharge of the hydrogel at the nozzle modules 310, 350. Basic data for this may be transmitted from the outside through wired/wireless data communication, or through a storage means such as a USB or the like.

Further, the control unit 400 may have a temperature control algorithm by which a raw material forming temperature or heater operation temperature of the former 300, or an operation temperature of a platform heater (not shown) attached to a lower surface of the base 210 of the platform 200 is feedback controlled from a corresponding temperature sensor.

Further, the control unit 400 may move (e.g., elevate or descend) the base 210 by controlling the driving motor 223 of the z-axis linear driving device 221 of the platform 200 during the relative movement corresponding to the x-axis linear driving device (323) and the y-axis linear driving devices 321, 322. In other words, the nozzle modules 310, 350 of the former 300 and the base 210 of the platform 200 may be moved relative to each other.

The device 10 for producing a skin care pack using hydrogel of the embodiment may take a driving type of a Cartesian type 3D printer which has an optimal structure so as to produce a hydrogel mask pack based on raised temperature forming. Further, the device 10 for producing a skin care pack using hydrogel is configured to discharge a raw material in an extruding method by a pump such as a peristaltic pump which can prevent leakage of hydrogel without a separate valve. The device 10 for producing a skin care pack using hydrogel of the embodiment may include a detailed configuration to be described later for rapidly and accurately embodying customized mask pack production.

For example, the housing 100 may have a box-shaped wall structure. The housing 100 may be surrounded by exterior material suitable for a cosmetic producing device, and be provided with a thermal insulating material (not shown) installed within the wall as an interior material.

As shown in FIG. 2, the housing 100 includes a rear wall 103 which is assembled or erected on the floor plate 102 so as to correspond to a boundary position of the work space 101. A power connector (not shown) connected to a power source terminal of the control unit 400 may be installed behind the rear wall 103.

Further, the housing 100 may include a pair of side walls 104, 105 which are connected to both sides of the rear wall 103 and erected on the floor plate 102. Also, the housing 100 may include a ceiling wall 106 connected to upper ends of the pair of side walls 104, 105 and the rear wall 103, and the front of the housing 100 may be opened. Here, the floor plate 102 of the housing 100 may be combined to lower surfaces of the rear wall 103 and the side walls 104, 105 by using a plurality of bolts.

Further, in order to replace the syringe or take out a mask pack, the front of the housing 100 and the work space 101 may be selectively closed or opened correspondingly to opening and closing operation of the door 110 (e.g., rotation around a rotational axis of an x-axis direction). For the purpose of this, the housing 100 may include a tension gas spring 120 installed between the door 110 hinge-combined to the ceiling wall 106, and a front surface of the side surface 104. The tension gas spring 120 functions to maintain an open state of the door 110 by supporting it at the time of rotational opening of the door 110, or to help the door 110 to be opened and closed smoothly. Further, the tension gas spring 120 may damp a shock at the time of closing of the door 110.

Also, the housing 100 may include a control unit casing 107 which is integrally connected to an outer side of the right side wall 104, and which exposes an input/output display device of the control unit 400 to the front direction of the housing 100.

The control unit casing 107 may be a control box including a power supply device, an electronic circuit device for control, or the like. In addition, there may be a cable passage 108 on the right side wall 104 of the housing 100 for spatially connecting an inner space of the control unit casing 107 and the work space 101 to each other.

Further, the housing 100 may include a driving device protection cover 130 installed at the floor plate 102 of the housing 100 so as to cover a lower portion of a linear driving device 221 of the platform 200 and a lower portion of linear driving devices 321, 322, 323 of the former 300.

The driving device protection cover 130 may be a cap structure having partially penetrated areas 134, 135, and may prevent a portion of raw material or foreign material from entering a rail or operation region of the linear driving devices 321, 322, 323 and causing a device failure.

For the purpose of this, parts located at lower portions of the y-axis linear driving devices 321, 322 and the z-axis linear driving device 221 may be placed in an inner space of the driving device protection cover 130. Contrarily, moving parts of the y-axis linear driving devices 321, 322 and the z-axis linear driving device 221, and payload objects loaded on the moving parts thereof (e.g., the base 210, the x-axis linear driving device 323, the discharge unit H) may be placed above the driving device protection cover 130 through the penetrated areas 134, 135 formed on an upper surface of the driving device protection cover 130. Like this, the linear driving devices 221, 321, 322, 323 are configured to be separated into two axes (e.g., x-y axis) and one axis (e.g., z axis), and thus it can stably produce a 3D skin care pack or mask pack while relatively increasing accuracy of repeated movement of the discharge unit H.

Further, in a lower surface of the driving device protection cover 130, a plurality of bolt holes (not shown) may be formed for being combined to bolts installed on the floor plate 102.

Also, the driving device protection cover 130 may be constituted by a front cover portion 131 and a rear cover portion 132 which can be assembled or disassembled for installation and maintenance of the platform 200 or the former 300.

On both cover wall portions at which the front cover portion 131 and the rear cover portion 132 confront to each other, a recessed portion or a protruding portion 133, such as concave and convex shapes, which can be engaged to each other, may be formed. As a result, the engagement and contact between the front cover portion 131 and the rear cover portion 132 can be made tightly.

In particular, the front cover portion 131 of the driving device protection cover 130 may include a residue collecting receptacle 137 with a mouth portion opened toward the z-axis direction for collecting residues which are generated when washing the nozzle of the former 300. Specifically, an installation hole 136 may be formed on the upper surface of the front cover portion 131. The residue collecting receptacle 137 may be detachably inserted or installed into the installation hole 136.

As a user can separate and wash the residue collecting receptacle 137, it is possible to perform maintenance and maintain cleanness with ease. Further, nozzle clogging resulting from replacement of a raw material may be prevented in advance.

Referring to FIG. 1 or 2, the platform 200 may include the z-axis linear driving device 221 which is installed on the floor plate 102 of the housing 100, and which is driven according to a control signal provided from the control unit 400. In the embodiment, the z-axis linear driving device 221 is described by way of example as being provided on the platform 200 for 3D printing, but the z-axis linear driving device 221 may be provided on the former according to an embodiment.

Also, the platform 200 includes the base 210 which is ascended or descended along the z-axis direction by the z-axis linear driving device 221, and which is disposed above the driving device protection cover 130 of the work space 101 of the housing 100, and a plurality of film holders 230.

A plurality (e.g., two) of films 20 may be placed on the base 210. The film 20 may be fixed or separated by a plurality of film holders 230 which can be attached or detached with respect to the base 210 by means of a magnetic force.

For example, if a mask pack is constituted by two segments correspondingly to an upper and lower portions of a user's head, there may be two pattern parts. That is, the pattern part may be made on each film 20. That is, this embodiment has an advantage that it is possible to precisely produce a hydrogel skin care pack which is divided into a plurality of the pattern parts correspondingly to a three-dimensional face shape of a user.

Meanwhile, a discharge path of hydrogel for forming a mask pack may be set to be discontinuous. That is, one segment of a mask pack formed on one film 20 has a plurality of portions connected to each other, and when each portion is continuously formed and one portion is formed to be discontinuous with another portion, the one portion and the other portion are connected to each other after a predetermined period of time has elapsed.

FIG. 13 is a plan view of a segment produced by the device shown in FIG. 1.

For example, referring to FIG. 13, one segment S of a mask pack, which finally has one shape, may be formed by forming portions A and B separately and discontinuously. In this regard, the portion A and the portion B may be each formed continuously. That is, in a case where the former 300 forms the portion B after the portion A has been formed by continuously discharging hydrogel for forming the portion A, the portion B begins to be continuously formed not from a line P1-P2, which is a boundary line between the portions A and B, but from, for example, a point P3, which is another point in the portion B except the boundary line. In this case, the forming of the portion B may be finished at the line P1-P2, by which the portions A and B can be connected to each other, thus finally forming an integral one segment.

Here, it is obvious that the line P1-P2, which is a boundary between the portions A and B, and the point P3 are all exemplary.

However, the hydrogel to be discharged from the former 300 has been heated, thereby having a low viscosity, and the hydrogel begins to be cooled from when it is discharged from the nozzle modules 310, 350, whereby hydrogel is gradually hardened. At this time, if the portions A and B are discontinuously formed as described above, and the portions A and B are connected after a period of time (time spent on forming the portion B) has elapsed after the portion A has been formed, there may occur a problem that, since the portion A which has been already formed is relatively more hardened, the portions A and B are not well connected to each other at the line P1-P2.

In the embodiment, in order to prevent this problem, there is further provided the heater 240 for heating the base 210 on which hydrogel is seated and formed. That is, the heater 240 may provide heat to the base 210 to prevent the hydrogel discharged on the base 210 from being hardened or to heat the hydrogel, and for example, the temperature of the base 210 may be kept at 20° C. Here, the temperature of the base 210 may be lower than that of the hydrogel discharged from the nozzle module 310, 350.

With this, until the portion B is formed from the point P3 and connected to the portion A with the line P1-P2 line after the portion A has been formed, the portion A is not hardened and can maintain its viscosity to a certain level, which results in that the portions A and B are surely connected to each other, thereby being possible to obtain an integrated segment.

The former 300 may move the nozzle modules 310, 350 in an x-axis and y-axis direction.

The former 300 may include the two y-axis linear driving devices 321, 322 and the one x-axis linear driving device 323, which are controlled by the control unit 400 as described above so as to operate in linkage with the platform 200. These linear driving devices 321, 322, 323 may be linear motors.

For example, the two y-axis linear driving devices 321, 322 for the former 300 may be parallelly disposed on the floor plate 102 of the housing 100 except an area where the platform 300 is installed. As the two y-axis linear driving devices 321, 322 are parallelly disposed, the payload of the x-axis linear driving device 323 and inertial force caused by its movement can be stably supported, so that the mask pack production can be precisely performed.

Also, the x-axis linear driving device 323 for the former 300 may be moved by the y-axis linear driving devices 321, 322.

Further, at least one nozzle module 310, 350, which corresponds to the discharge unit H, may be moved based on a moving plate (not shown) of the x-axis linear driving device 323 and the mount block 327 combined to the moving plate.

These nozzle modules 310, 350 are configured as the discharge unit H of the former 300 to satisfy requirements of a hydrogel discharge device. Here, the requirements of the hydrogel discharge device may mean convenience of charging and replacing a raw material, heating performance of a syringe, a tube and a nozzle for melting hydrogel, extrusion performance of a fixed amount of hydrogel, and maintenance convenience (e.g., washing and nozzle replacement).

The nozzle modules 310, 350 may be symmetrically arranged, and play a role of discharging toward the platform 200 the hydrogel as a raw material for producing a mask pack.

FIG. 4 is a perspective view of the nozzle module of the discharge unit shown in FIG. 3, and FIG. 5 is an exploded perspective view of the nozzle module shown in FIG. 4. Further, FIG. 6 is a front view of the nozzle module shown in FIG. 4, FIG. 7 is a cross-sectional view taken along a line C-C shown in FIG. 6.

Referring to FIGS. 3 to 7, the angle member 328 of the nozzle module 310 may include an attachment plate 328a which surface-contacts a front surface of the mount block 327 and has a plurality of installation holes; a connection plate 328b which surface-contacts a side surface of the main block 330 of the nozzle module 310 and has a plurality of connection holes; and a cutaway portion 328c formed in the connection plate 328b based on between the connection holes.

The nozzle modules 310, 350 may include a syringe 312, a nozzle 311, and a pump 340.

As the nozzle modules 310, 350 may be provided left-right symmetrically, the detailed configuration thereof will be explained based on the nozzle module 310 located right in order to avoid repeated explanation in the description below.

Specifically, the nozzle module 310 may include the pump 340 which is a peristaltic pump capable of performing ultra-precise fixed amount discharge in an extrusion manner for a raw material such as hydrogel, so that it can be configured to be capable of continuously discharging a raw material while satisfying heating condition suitable to properties of the raw material, such as hydrogel or the like, and not to leak a raw material of a low viscosity through the nozzle 311. So, a mask pack can be rapidly and precisely produced.

In detail, the nozzle module 310 may include the syringe 312 which stores a raw material, and the main block 330.

First, the syringe 312, as a replaceable cartridge capable of being attached to or detached from the nozzle module 310, corresponds to a raw material storage means.

Further, the nozzle 311 of the nozzle module 310 is disposed spaced apart under the syringe 312. In this case, the nozzle 311 is detachably combined to a raw material discharge hole of the main block 330. If a hole of the nozzle 311 is clogged, or if its replacement is needed, the nozzle 311 may be detached from the raw material discharge hole of the main block 330 by a user or a maintenance worker.

The main block 330 may be disposed between the nozzle 311 and the syringe 312. The main block 330 may become a support base of the nozzle 311, the syringe 312, and the angle member 328, and provide a raw material flow path 331.

The nozzle module 310 includes the pump 340 which is installed to the main block 330 so as to be communicated to the raw material flow path 331 of the main block 330, and which pumps a raw material of the syringe 312 to supply the same toward the nozzle 311.

Here, the pump 340 may include a pump bracket 349 which becomes a support base of the tube housing 344 of the pump motor 346 for mounting the pump motor 346 on the main block 330, and to which the cooling housing 510 is combined.

That is, the pump 340 may be connected to the main block 330 through a pump bracket 349, and receive heat transfer from the main block 330 or the heater 332.

The pump bracket 349 may become a support base or an installation position of the tube housing 344. As one example, the tube housing 344 may closely contact and be combined to the pump bracket 349 using a plurality of installation bolts (not shown).

For the purpose of this, the peristaltic pump, that is, the pump 340 may be disposed at a lateral one side of the main block 330 vertical to the extension direction (e.g., gravity direction) of the syringe 312 and nozzle 311.

Further, the raw material flow path 331 may be heated by the heater 332. Further, the control unit 400 may control the heater 332 so that temperature of the main block 330 measured by a temperature sensor 333 to be described below can be maintained to a predetermined range.

Further, heat of the heater 332 may be transferred to a tube 341 of the pump 340, the nozzle 311, and a syringe heating block 334 through the main block 330 to which the one heater 332 is installed. Therefore, temperature of hydrogel, a raw material, can be stably maintained to a requirement value necessary for skin care pack production, and heat transfer efficiency can be maximized.

The pump 340 may be a peristaltic pump so that a raw material which is heated by the heater 332 cannot be leaked from the nozzle 311 or can satisfy the above-described hydrogel discharge device requirements. That is, the pump 340 may avoid cross contamination between a raw material to be discharged and the pump 340, enable complete self-priming pumping operation thereof, and make safe run-dry possible without any damage to the pump 340. Further, the pump 340 needs neither a valve nor a seal, and pumping operation is smooth. So, it can be very ideal to delivering hydrogel which is sensitive to deformation.

Also, as the pump 340 itself performs a role of temporarily stopping flow of a raw material necessary for forming a mask pack when the operation of the pump 340 is stopped, the reverse flow of a raw material at the time of stopping the operation of the pump 340 can be prevented without any separate valve device, and the leakage of a raw material can be prevented in advance. That is, the embodiment can prevent a raw material, such as hydrogel, for producing a mask pack from being leaked from the pump 340 in advance.

Further, the temperature sensor 333 and the heater 332 for generating heat of heating conditions of a raw material or providing such heat to a raw material may be installed to the main block 330. The heater 332 basically heats the main block 330 and various constituting elements connected with respect to the main block 330. For example, the heater 332 may perform heating operation to a temperature of the heating conditions (e.g., 70° C. to 95° C.) for decreasing viscosity of a raw material for mask pack production, such as hydrogel, on entire regions of an extruding section, such as the main block 330, the nozzle 311, the tube 341 of the pump 340, the syringe heating block 334 and the syringe 312.

For example, the heater 332 may be configured to apply heat to the syringe heating block 334, the main block 330, the syringe 312, the nozzle 311 and the nozzle joint 311. Thanks to this, heat can be preserved in a rear portion of the syringe 312 in which a raw material is contained and a conveying section of a raw material, so that optimized viscosity can be maintained.

If a raw material is heated to a temperature of the heating condition or lower via the heater 332, it is difficult to perform conveying action for extrusion because of high viscosity, whereas if it is heated to a temperature of the heating condition or higher, there may occur degraded extrusion because air bubbles are generated due to evaporation of moisture of a raw material. For example, the raw material may maintain a viscosity ranging from 120 CPS to 2,500 CPS at a temperature ranging from 70° C. to 95° C., which enables the discharge through the nozzle. However, if it is heated to 100° C. or higher, a problem that water which is one of components of the raw material is evaporated may occur. So, it is preferable to set the temperature of the raw material to be 95° C. or lower for the purpose of safety.

The main block 330 is disposed at a central position of three directions with regard to the syringe 312, the nozzle 311 and the pump 340 which are connected to the main block 330 in each of the directions. Therefore, heat of the main block 330 can be transferred evenly to the syringe 312, the nozzle 311 and the pump 340.

In particular, as a highest temperature ambience is formed at a lower side of the syringe 312 by the heater 332, hydrogel which is contained in the syringe 312 at a low viscosity also forms a highest temperature ambience at the lower side of the syringe 312. Due to this, convection currents occur in the hydrogel within the syringe 312, resulting in that the entire hydrogel in the syringe 312 has a similar heating state. Therefore, the viscosity of hydrogel discharged through the syringe 312 can be maintained uniform, and thereby quality of forming a mask pack and quality of a final product can be improved.

Further, there may be provided a cooling device 500 which is a means of preventing the pump motor 346 from being overheated by the heat transferred toward the pump 340. The device 10 for producing a skin care pack according to the embodiment may be installed in a store and driven continuously for several hours. In this case, the pump motor 346 may be overheated, which in turn may lead to malfunction and failure of the pump 340. In order to prevent this, there may be provided the cooling device 500 at a side of the pump 340, and the cooling device 500 may cool the pump motor 346 by be operated according to a predetermined algorithm. The nozzle module 310 having the main block 330 and the pump 340 can maintain an appropriate operation temperature with the aid of the cooling device 500 under a situation of discharging hydrogel, and in particular, protect the pump motor 346 of the pump 340 from thermal load.

For example, the cooling device 500 may include a cooling fan 520 which is disposed at a side of the main block 330 or disposed at a side of the pump motor 346 and generates a flow toward the pump 340; and a fan motor 521 which rotates the cooling fan 520. Here, the pump motor 346 may be cooled by the flow generated at the cooling fan 520. Further, the cooling device 500 may discharge into the work space 101 the flow which has absorbed heat from the pump motor 346.

The above-described control unit 400 may control a rotational speed of the cooling fan 520 via the fan motor 521.

Further, as the temperature sensor 333 is installed in the main block 330 based on a position adjacent the heater 332, a temperature value which is measured through the temperature sensor 333 and input toward the control unit 400 may be used relatively precisely to perceive the heating condition of a raw material.

Meanwhile, the raw material flow path 331 of the main block 330 may be configured to turn the raw material discharged from the upper side syringe 312 to a side direction and transfer the same toward the pump 340 side, and turn the raw material discharged from the lateral side pump 340 to a downward direction and turn the same to the nozzle 311, and be connected to the U-shaped flexible tube 341 of the pump 340.

There may be provided quick couplers for tube piping at connection points between both ends of the tube 341 and the raw material flow path 331, and thus it is possible to easily replace the tube 341.

The tube 341 may be installed at the pump 340 based on a gap between a plurality (e.g., ten) of rollers 342, 343 in the pump 340 and a tube housing 344 so that it can be pressed to be deformed or restored by the rollers 342, 343 of the pump 340.

This pump 340 is connected to the raw material flow path 331 of the main block 330, and includes the tube 341 having a section of a U shape.

Further, the pump 340 includes a pump head 347 which is covered by the U-shaped section of the tube 341 and contacts the tube 341 and which is provide with a plurality of rollers 342, 343 that have an arrangement configuration in which a gap between the rollers 342, 343 is relatively narrow.

With the rollers 342, 342 of the narrow arrangement configuration, hydrogel can be discharged from the nozzle 311 precisely and quickly, and as a result the fixed amount distribution of hydrogel can be realized during the mask pack producing process.

Also, the pump 340 includes a pump motor 346 which has a shaft 346a for rotating the pump head 347 combined to the pump head 347. The pump motor 346 may be a servo motor or a step motor, and rotational speed or rotation angle of pump head 347 can be finely adjusted by the above-described control unit 400.

Further, the pump 340 includes a pump bracket 349 for mounting the pump motor 346 to the main block 330.

A plurality of first mount protrusions 349a having a fastening hole may be formed on an upper portion of the pump bracket 349, and by these first mount protrusions 349a, the cooling device 500 may be disposed at the upper portion position of the pump motor 346. Here, the cooling device 500 may play a role of preventing beforehand the pump motor 346 from being damaged by a fire or failing to operate due to overheat.

Further, a plurality of second mount protrusions 349b having an installation hole may be formed on a lower portion of the pump bracket 349, and by these second mount protrusions 349b, a cooling housing 510 of the cooling device 500 may be mounted. Also, a third mount protrusion 349c at a side portion of the pump bracket 349 may have a connection hole and thus be combined to the main block 300 side by a fastening bolt (not shown).

Like this, the pump bracket 349 enables the cooling device 500 and the pump 340 to be mounted and disassembled easily, through which the maintenance can be easily performed.

For example, if repair or maintenance for the pump 340 is needed, only the tube 341 can be replaced, and thus there is an effect of shortening time for maintenance and reducing cost for it.

Further, the tube housing 344 may have a C-block shape which may be included in the pump 340 and which may support and guide a tube. In the tube housing 344, a side portion facing the tube 341 may be opened. The tube housing 344 may be installed at the pump bracket 349 based on the U-shaped section of the tube 341. In this case, a guide surface of an inner side of the tube housing 344 may be disposed at an outer side of the U-shaped section of the tube 341. Therefore, the tube housing 344 may play a role of supporting the tube 341 which is pressed by the roller 342, 343 when the pump head 347 is rotated.

Here, the tube housing 344 may be formed of a Teflon material, which can prevent heat generated at the heater 332 from being transferred to the pump motor 346 by blocking heat transfer to outside.

The pump head 347 of this pump 340 includes a first disc 347a which is combined to the shaft 346a of the pump motor 346 in such a manner that it does not contact the guide surface of the tube housing 344. Further, the pump head 347 may include a plurality of roller pins 347b which are arranged along the circumference direction in the first disc 347a and which serve as a rotation base of the rollers 342, 343 while arranging the rollers 342, 343 in a plurality of layers along the pin extension direction; and a second disc 347c which has a plurality of connection holes combined to end portions of these roller pins 347b and which has the same diameter as that of the first disc 347a.

In this case, each roller 342, 343 may be rotatably installed at the roller pin 347b through a bearing 343a disposed on an inner circumferential portion of the roller. Therefore, even when the rollers 342, 343 are rotated in contact with the tube 341, smooth rotation of the roller 342, 343 can be guaranteed, and noise generated by the rotation of the rollers 342, 343 can be minimized.

Further, the number (e.g. ten) of rollers 342, 343 may be an optimized value for minimizing pulsation which can be generated when a raw material for producing a mask pack, such as hydrogel, is conveyed or pumped, in view of the operation speed of the former 300.

Further, a diameter of the tube 341, a thickness of a tubular wall of the tube 341 or the like may be determined correspondingly to a raw material for producing a mask pack and the numbers of and disposition gap between the rollers 342, 343.

The rotation and revolution of the rollers 342, 343 may press the tube 341 in a diameter direction of the tube 341, and as a result, inner surfaces of the pressed tube 341 may be brought into close contact with each other, so that movement of a raw material in the tube 341 can be blocked. Rotational force of the pump head 347 by the pump motor 346 of the pump 340 may be converted to suction and flow forces of a raw material, such as hydrogel or the like.

That is, the rollers 342, 343 may be moved along the rotational direction of the pump head 347 correspondingly to the rotation of the pump head 347. As the rollers 342, 343 are moved, the compressed tube 341 is restored to its original shape, and as a result, suction and flow of the raw material is accomplished by a negative pressure generated in the tube 341.

That is, as a raw material as much as a flow rate corresponding to a space between the rollers 342, 343 is repeatedly collected in the tube 341, the conveyance of the raw material can be accomplished from the inside of the syringe 312 to the nozzle 311 by way of the raw material flow path 331 of the main block 330 and the tube 341.

A syringe joint 380 may be laid as a pipe between an upper surface hole of the raw material flow path 331 of the main block 330 and the syringe 312. In this case, for the purpose of easiness of replacement of the syringe 312, an upper end of the syringe joint 380 may be screw-coupled to the syringe 312 so as to be assembled or disassembled, while a lower end of the syringe joint 380 may be tightly screw-coupled to the upper surface hole of the raw material flow path 331 of the main block 330.

Further, a nozzle joint 381 may be installed between a lower surface hole of the raw material flow path 331 of the main block 330 and the nozzle 311. In this case, for the purpose of easiness of replacement of the nozzle 311, an upper end of the nozzle joint 381 may be screw-coupled to a lower surface hole of the raw material flow path 331 of the main block 330, while a lower end of the nozzle joint 381 may be coupled with the nozzle 311 in a simple press-fit manner. Therefore, if the replacement of the nozzle 311 is needed, a user may extract the nozzle 311 from the nozzle joint 381, and insert a new nozzle (not shown) into the nozzle joint 381.

Meanwhile, the nozzle module 310 may include the syringe heating block 334 which is erectly combined to and extended upward from a top plate 330a of the main block 330, and which has a first semi-circular recessed portion 334a in contact with an outer circumferential surface of a side of the syringe 312.

Here, the top plate 330a is a U-shaped plate member, and the syringe joint 380 may be disposed in a U-shaped space of the top plate 330a.

Further, the nozzle module 310 may include a syringe cover block 335 which is disposed opposite the syringe heating block 334 with reference to the syringe 312, and which has a second semi-circular recessed portion 335a in contact with an outer circumferential surface of another side of the syringe 312.

Further, the nozzle module 310 may include an elastic member 337 which generates an elastic force in such a manner that the syringe cover block 335 can be moved toward the syringe heating block 334 relative to the syringe 312 (e.g., adjusting a gap by use of a spring elastic force), and a coupling member 338 which combines the syringe cover block 335 and the syringe heating block 334 by way of the elastic member 337. The number of elastic members 337 and the number of the coupling members 338 may be the same as the number of guide holes formed in the corner positions of the syringe heating block 334.

Here, the coupling member 338 may be a bolt, a tightening screw or the like. Further, the elastic member 337 may be a spring washer or a coil type compression spring. The elastic force of the elastic member 337 may be adjusted by tightening the coupling member 338.

In order to adjust the elastic force by means of this tightening, a bolt screw thread of the coupling member 338 is fastened to a screw hole of the syringe cover block 335 after having penetrated through a spring hole of the elastic member 337 and a guide hole of the syringe heating block 334.

In this regard, the screw hole of the syringe cover block 335 faces the syringe heating block 334, and is formed at every corner portion corresponding to the guide hole.

Further, the guide holes of the syringe heating block 334 are formed at four corners of the syringe heating block 334 respectively based on a thickness direction of the syringe heating block 334, and a stepped portion is formed along the circumferential direction in the guide hole.

Therefore, after the elastic member 337 has been inserted into the guide hole of the syringe heating block 334, it can be supported onto the stepped portion in the guide hole. Further, diameters of a bolt head of the coupling member 338 and the elastic member 337 are smaller than that of the guide hole of the syringe heating block 334. Accordingly, the coupling member 338 and the elastic member 337 may be disposed in the guide hole of the syringe heating block 334 so as to be moved along the guide hole. Further, a left end portion of the elastic member 337 disposed in the guide hole contacts and is supported onto the bolt head of the coupling member 338, and the left end portion of the elastic member 337 contacts and is supported onto the stepped portion in the guide hole.

In such a state, when a certain external force (e.g., a user's finger force or a divided force resulting from the inclined direction insertion of the syringe 312) is applied in a direction in which the syringe cover block 335 is moved away from the syringe heating block 334, the coupling member 338 screw-coupled to syringe cover block 335 is also moved together with the syringe cover block 335. As a result, the bolt head of the coupling member 338 compresses the elastic member 337, so that an elastic resilient force can be generated.

As shown in FIG. 4, a gap G which the coupling member 338 and the elastic member 337 are to adjust may mean a clearance space between the syringe cover block 335 and the syringe heating block 334 in relation to a state where they are in close contact with the syringe 312.

Therefore, although a user installs the syringe 312 slantly while not aligning the insertion direction of the syringe 312 with the z-axis, the gap G can be adjusted by the coupling member 338 and the elastic member 337.

For example, when the syringe 312 is inserted slantly, the outer surface of the syringe 312 contacts an upper periphery of an inner circumferential surface of the second semi-circular recessed portion 335a of the syringe cover block 335, and consequently the syringe cover block 335 can be moved in a direction away from the syringe heating block 334. In this case, the coupling member 338 may guide the movement of the syringe cover block 335 while at the same time the elastic member 337 is compressed and generates the elastic resilient force as described above.

The syringe 312 may be installed at the syringe joint 380 by screw rotation, which makes a state where a raw material of hydrogel or the like of the syringe 312 can flow to the raw material flow path 331 by way of the syringe joint 380.

Meanwhile, after the installation of the syringe 312, the coupling member 338 and the syringe cover block 335 may return in a direction in which they approach the syringe heating block 334 as they are restored into an original shape by an elastic resilient force of the elastic member 337. As a result, the inner circumferential surface of the second semi-circular recessed portion 335a of the syringe cover block 335 can be brought into close contact to the outer surface of the syringe 412.

With this, the syringe 312 can be easily disposed and installed at a space (e.g., a syringe insertion hole) between the first semi-circular recessed portion 334a of the syringe heating block 334 and the second semi-circular recessed portion 335a of the syringe cover block 335.

In other words, a user can easily replace the syringe 312, and the thus replaced syringe 312 is brought into close contact with the inner circumferential surfaces of the first semi-circular recessed portion 334a of the syringe heating block 334 and the second semi-circular recessed portion 335a of the syringe cover block 335 by means of an elastic force or elastic resilient force of the elastic member 337. So, the heat transfer from the syringe heating block 334 to the syringe 312 can be effectively accomplished.

That is, the syringe cover block 335 and the syringe heating block 334 form a syringe insertion hole therein with the first and second semi-circular recessed portions 334a, 335a, and the syringe 312 can be inserted or separated through the syringe insertion hole. As a result, the replacement of the syringe 312 can be performed easily and rapidly.

Particularly, the syringe cover block 335 may include a skirt plate portion 335b which is integrally extended from a lower surface of the second semi-circular recessed portion 335a and protects the front surface of the main block 330 in a non-contact state. Here, there is an advantage that the skirt plate portion 335b can be a protecting means of the pump 340 or the main block 330.

Also, a slit 336 for checking raw material remainder quantity in the syringe 312 is formed in the syringe cover block 335 so as to penetrate the syringe cover block 335 in a thickness direction. Since a casing of the syringe 312 is a transparent or semi-transparent material, a user can intuitively check the remainder quantity of a raw material in the syringe 312 with user's naked eyes. That is, the slit 336 can provide intuitive and excellent visibility to a user.

Here, the syringe cover block 335 may be formed with a Teflon material having a low thermal conductivity. By this, the heat inside the syringe 312 can be well preserved.

Hereinafter, detailed configuration and operation of the cooling device 500 according to the embodiment will be described.

As described above, the nozzle module 310 has the cooling fan 520 disposed on an upper portion of the pump motor 346 of the pump 340 which discharges hydrogel. As the pump motor 346 may be cooled by the flow generated at the cooling fan 520, the device 10 for producing a skin care pack can be stably used for a long period of time. Here, the flow discharged from the cooling device 500 may be discharged to the work space 101 of the housing 100 by way of the pump motor 346.

The cooling device 500 may include a fan motor 521 which is disposed beside the syringe heating block 334, which is electrically connected to the control unit 400, and which rotates the cooling fan 520. Here, the fan motor 521 may be direct current electric motor having an excellent heat-resistance performance, and is configured to be self-cooled by the rotation of the cooling fan 520. Further, the fan motor 521 may be a variable speed motor in which a pulse width modulation or integrated circuit driving chip for controlling a motor speed is mounted. Therefore, the cooling fan 520 may be rotated at a low or high speed, or stopped correspondingly to an operational signal of the control unit 400 depending on temperature change at the time of heat exchange.

Further, the cooling device 500 includes a housing cover 530 which can be detachably connected to the first mount protrusion 349a of the pump bracket 349 by means of a fastening means, such as a bolt. At this time, the fan motor 521 may be installed in the housing cover 530. Further, the housing cover 530 may be fixed to the cooling housing 510. Further, the cooling fan 520 may generate flow in a space formed by the cooling housing 510 and the housing cover 530. At this time, the cooling fan 520 may be accommodated inside the cooling housing 510.

As described above, the cooling device 500 may include the housing cover 530 which is connected to the first mount protrusion 349a, and at which the fan motor 521 and cooling fan 520 for generating flow are installed; and the cooling housing 510 providing a space in which the cooling fan 520 is accommodated, so that flow is formed. At this time, the housing cover 530 may be combined to the first mount protrusion 349a, the main block 330 may be combined to the third mount protrusion 349c, and the cooling housing 510 may be combined to the second mount protrusion 349b.

As shown in FIG. 7, the housing cover 530 has a fan aperture 531 and a plurality of bolt holes 532. Here, the fan aperture 531 may have such a size allowing a motor shaft of the fan motor 521 or the cooling fan 520 to be passed therethrough. Further, the bolt hole 532 may be used to install or fix the fan motor 521 by means of a bolt (not shown) with the fan motor 521 disposed outside the housing cover 530.

Like this, the fan motor 521, which is included by the cooling device 500, may be installed at the housing cover 530 based on the bolt hole 532 with the motor shaft of the fan motor 521 disposed at the center of the fan aperture 531.

Also, there may be provided the cooling fan 520 to the cooling device 500, which is combined to the motor shaft of the fan motor 521 and which is disposed spaced apart from the upper portion of the pump motor 346. As one example, the cooling fan 520 may be a centrifugal fan which intakes and discharges air in directions perpendicular to the motor shaft. In this case, it is possible to reduce an entire size of the cooling device 500, and thus it is possible to miniaturize the nozzle module 310 and the entire device.

When the cooling fan 520 is rotated by the fan motor 521, compressed air may be generated. The compressed air generated from the cooling fan 520 like this passes by an outer surface of the pump motor 346 while performing heat exchange with heat of the pump motor 346, or heat of the neighboring components (e.g., main block 330, syringe heating block 334, and syringe cover block 335), thus performing cooling.

Particularly, the cooling device 500 may include the cooling housing 510 which can smoothly cause heat exchange by the compressed air. That is, the cooling housing 510 can guide flow generated by the cooling fan 520 of the cooling device 500.

The cooling housing 510 may be connected to the second mount protrusion 349b of the pump bracket 349 in a direction in which it faces the housing cover 530.

For example, the cooling housing 510 may become a boundary of a flow area of the compressed air while covering the pump motor 346, the cooling fan 520, the main block 330, some area of the syringe heating block 334, and some area of the syringe cover block 335.

The pump motor 346 may be accommodated in an inner space of the cooling housing 510.

The cooling housing 510 may guide the flow of the compressed air such that the compressed air generated from the cooling fan 520 can exit (A/OUT) through an air-discharge opening 511. That is, air which has absorbed heat of the pump motor 346 may be discharged into the work space 101 of the housing 100 through the air-discharge opening 511. Here, the air-discharge opening 511 may be opened toward a side. Further, the air-discharge opening 511 may be formed adjacent to the pump motor 346.

Further, the cooling housing 510 has an advantage of reducing fan rotation noise generated from the cooling fan 520 while protecting the cooling fan 520 by covering a neighboring space of the cooling fan 520 and the pump motor 346 except the air-discharge opening 511 or an intake opening 512 or a fine gap.

The air-discharge opening 511 of the cooling housing 510 may be opened in a half direction of the main block 330 with reference to the pump motor 346. Therefore, the air which has been heated relatively with the heat exchange may exit rapidly and smoothly through the air-discharge opening 511 without any separate obstacle, thus exhibiting an excellent heat exchange efficiency.

Further, the housing cover 530 may further include a plurality of connection terminal parts 402 for connection to an electric wire 401 extended from the control unit 400 to the nozzle module 410 in order to connect the fan motor 521, the heater 332, the pump motor 346 and the temperature sensor 333 to the control unit 400. Here, the connection terminal part 402 may be an electrically conductive or connecting device including a connector, a port, a connection pin, an electric wire connection hole or the like.

The lower part of the connection terminal part 402 may be disposed in a rotation area of the cooling fan 520 without being contacted therewith, and may be cooled by the compressed air of the cooling fan 520. Therefore, there is an effect of be possible to prevent overheating phenomena of a connection portion of the connection terminal part 402 and the electric wire 401 connected thereto.

The housing cover 530, which is a plate or a structure bent at a right angle, may include a horizontal plate part 533 at which the connection terminal part 402 is installed; and a vertical plate part 534 which is integrally bent at the horizontal plate part 533, and at which the fan motor 521 is installed.

The vertical plate part 534 of the housing cover 530 and the pump bracket 349 play a role of a barrier wall which divides an area where the pump head 347 and the tube 341 are located, from another area where the pump motor 346 and the cooling fan 520 are located.

Therefore, the heat of the area necessary for operation of the pump 340 cannot be excessively transferred to the other area of the cooling fan 520 and the pump motor 346. And, the compressed air generated in the cooling fan 520 can be efficiently used to cool down the pump motor 346.

The housing cover 530 may be fixed to the cooling housing 510 and the pump bracket 349 using a bolt or screw, or may be easily separated therefrom by disassembling the bolt or screw. Accordingly, the maintenance for the connection terminal part 402, the fan motor 521 or the like can be easily performed.

Referring to FIG. 5, the cooling housing 510 includes a lower surface wall 514 provided with a support rib 513 which closely contacts the second mount protrusion 349b of the pump bracket 349. At the support rib 513, there is formed a bolt fastening hole corresponding to a mount hole of the second mount protrusion 349b of the pump bracket 349.

Further, the cooling housing 510 includes a side wall 515 which extends from an end of the lower surface wall 514 and which is provided with the air-discharge opening 511 that is formed based on a position corresponding to the vertical height of the pump motor 346. At the side wall 515, there may also be formed a bolt or screw fastening part 515a. In this case, a bolt or screw for fastening the vertical plate part 534 of the housing cover 530 and the cooling housing 510 to each other can be fastened to the screw fastening part 515a, and as a result, the combination between the cooling housing 510 and the housing cover 530 can be more stable and firm.

Also, the cooling housing 510 includes another side wall 516 which extends vertically from another end of the lower surface wall 514 and which is provided with the intake opening 512 formed at the upper portion. For example, the intake opening 512 may be opened upward.

The air which is located outside the cooling housing 510 and thus has a lower temperature compared to the inside of the cooling housing 510 may flow into (A/IN) the inside of the cooling housing 510 through the intake opening 512. That is, the air in the work space 101 of the housing 100 may be sucked into the space in the cooling housing 510 through the intake opening 512.

Further, the cooling housing 510 includes a finish wall 517 which is integrally connected to peripheries of the lower surface wall 514, the side wall 515, and the other side wall 516.

Further, the cooling housing 510 may include a guide wall 518 which integrally protrudes from the finish wall 517 toward the vertical plate part 534 of the housing cover 530 and which guides the flow F (see FIG. 7) of the compressed air generated by the cooling fan 520.

The guide wall 518 may play a role of guiding the air sucked through the intake opening 512 so as to be discharged through the air-discharge opening 511 via the cooling fan 520.

The guide wall 518 includes a flap 518a extending toward the lower surface wall 514 from a lower part of the upper surface wall 519 and having a shape of a wall which is inclined toward the air-discharge opening 511 at an end of the guide wall 518. By this flap 518a, the flow F of the compressed air can be guided smoothly toward the air-discharge opening 511.

Also, the end of the guide wall 518 may be disposed spaced apart from the pump motor 346. Further, between the side surface of the cooling housing 510, and the guide wall 518 and the pump motor 346, there may be provided a space through which air can flow.

Here, the guide wall 518 is described by way of example as being formed on the cooling housing 510, but it is not limited to this. For example, the guide wall 518 may be formed on the housing cover 530.

Further, the cooling housing 510 may include a top surface wall 519 which is integrally formed at an upper part of the finish wall 517 while connecting the upper part of the guide wall 518 and the upper part of the other side wall 512.

Further, the cooling housing 510 may include a connection space 519a which is formed between the upper part of the side wall 515 and the upper part of the guide wall 518 based on the same level as the upper surface wall 519, for disposing the horizontal plate part 533 of the housing cover 530 therein.

In this regard, the connection space 519a may be formed so that its width corresponds to a width of the horizontal plate part 533 of the housing cover 530. Therefore, the horizontal plate part 533 of the housing cover 530 can be precisely combined to the connection space 519a disposed at the upper part of the cooling housing 510.

In an inner space of the opening 519a, the cooling fan 520 is disposed so as to be non-contact, and a space between the right surface of the guide wall 518 and the left wall of the other side wall 516 may be spatially connected to the intake opening 512 and become a large air storage space relative to a cross-sectional area of the intake opening 512. Therefore, the air of a lower temperature relative to the compressed air may be smoothly and continuously sucked through the intake opening 512 from the outside of the cooling housing 510, and may be changed into the compressed air by the cooling fan 520 after flowing into the cooling housing 510. This compressed air may exit smoothly through the air-discharge opening 511 after performing the heat exchange as described above. As a result, the cooling device 500 may exhibit an excellent heat exchange performance.

As such, the embodiment can continuously produce a skin care pack using hydrogel by adjusting or maintaining a heat load of the pump 340 within a certain temperature range by means of the cooling device 400 of the nozzle module 310.

Further, the flow generated by the cooling device 500 is discharged to the work space 101 through the air-discharge opening 511 of the cooling housing 510, which can cause convection currents in the work space 101. Since hydrogel has a property that it is rapidly hardened when temperature is lower than a certain temperature, temperature inside the work space 101 is necessary to be maintained to a certain temperature, and for this, the heater 240 (FIG. 9) may be provided to the platform 200. However, with the heater 240 provided to the platform 200, heat is transferred only to a lower surface of a mask pack which is formed on the film 20, so an upper surface of the mask pack, particularly, a surficial part may be slightly hardened. However, according to the embodiment, when the convection current is generated in the work space 101 by the flow discharged from the cooling device 500, the work space 101 can be maintained at a high temperature ambience, and thus the hardening phenomena of hydrogel can be prevented. Particularly, as the air discharged from the cooling device 500 has absorbed the heat of the pump motor 346, such effect as described above can be realized more excellently.

Meanwhile, this cooling device 500 may be driven according to a predetermined control algorithm. For example, the cooling device 500 may be driven at predetermined time intervals, or it may be driven when the time for which the pump 340 is continuously driven exceeds a predetermined level. Further, the driving of the cooling device 500 may be controlled according to a measurement of a temperature sensor for measuring temperature of the pump motor 346, which is separately provided, a measurement of a temperature sensor for measuring temperature of the work space 101, which is separately provided, a measurement of the temperature sensor 333 provided at the main block 330 or the like.

In other words, the cooling device 500 may be driven depending on a predetermined condition, and the term of depending on the predetermined condition may be understood as being controlled according to one or more of the cooling device being driven at predetermined time intervals, the time for which the pump 340, which is a peristaltic pump, is continuously driven deviating from a predetermined range, temperature of the motor of the peristaltic pump, that is the pump motor 346 deviating from a predetermined range, temperature of the work space 101 deviating from a predetermined range, and temperature of the main block 330 deviating from a predetermined range.

Hereinafter, the platform 200 will be described in detail.

FIG. 8 is an enlarged perspective view of the platform shown in FIG. 2, and FIG. 9 is a perspective view showing a lower surface of the platform shown in FIG. 8. Further, FIG. 10 is an exploded perspective view of the platform shown in FIG. 8. Additionally, FIG. 11 is a front view of the platform shown in FIG. 8, and FIG. 12 is a cross-sectional view taken along a line D-D shown in FIG. 11.

Referring to FIGS. 8 to 12, the platform 200 may support with the base 210 a film 20 on which hydrogel (not shown) is discharged, and may include a z-axis linear driving device 221 which can move (e.g., elevate or descend) hydrogel, the film 20, the base 210, and the heater 240 disposed on a lower surface of the base 210 while moves relatively to the operation of the former 300.

That is, the z-axis linear driving device 221 of the platform 200 may include a bottom block 222 which is horizontally installed at the floor plate 102 of the housing 100 shown in FIG. 2.

The bottom block 222 may include a first sub-block 222c which protrudes in a side direction of the bottom block 222 for the disposition of a driving motor 223; a second sub-block 222d which integrally extends from the first sub-block 222c; and third sub-blocks 222e of a U-shaped cross-sectional shape which are integrally formed on both sides of the second sub-block 222d.

At the first sub-block 222c, there may be provided a plurality of holes for installing the driving motor 223.

In the second sub-block 222d, there may be provided a bearing seat part for installing a bearing 222a for a ball screw shaft 224. Further, on a lower surface of the second sub-block 222d, there may be provided a disposition space 222b of a driving force transmission mechanism. Here, the driving force transmission mechanism may include a driving pulley 223a for the driving motor 223, a belt 223b, and a driven pulley 223c. Also, the disposition space 222b provides an advantage of reducing weight or thickness of the bottom block 222.

In the third sub-block 222e, there may be provided a plurality of holes for erecting and fixing guide bars 225.

On the surface of the third sub-block 222e on which the guide bar 225 is located, there may be provided a groove for accommodating the guide block 226. With this, structure of the z-axis linear driving device 221 can be simply configured, and the interference between the guide block 226 and the third sub-block 222e can be reduced, thus showing an effect of obtaining a stroke of a movable frame 250.

In the third sub-block 222e and the second sub-block 222d, there may be provided a plurality of holes in order to reduce the weight of the bottom block 222 or enable tools for maintenance or the like to pass through.

Further, the lower surface of the third sub-block 222e of the bottom block 222 may closely contact the floor plate 102 of the housing 100, and the combination of the bottom block 222 and the floor plate 102 can be firmly maintained.

The z-axis linear driving device 221 of the platform 200 may include the driving motor 223 disposed at a side of the bottom block 222; the ball screw shaft 224 to which rotational force R of the driving motor 223 is transmitted, and which is rotatably combined based on the bottom block 222; the plurality of guide bars 225 dispersedly disposed at a plurality of points on the bottom block 222 with reference to the ball screw shaft 224; and guide blocks 226 slidably combined to the guide bars 225 respectively.

At both ends of the guide bar 225, there may be provided respective fastening holes. The both ends of the guide bar 225 may be combined between the bottom block 222 and a fixed frame 270 by means of the fastening hole and a bolt.

The driving motor 223 may be a step motor or servo motor which can adjust a rotational angle of the ball screw shaft 224.

The shaft of the driving motor 223 is axially combined to the driving pulley 223a. The ball screw shaft 224 may be axially combined to the driven pulley 223c. The belt 223b interconnects the driving pulley 223a and the driven pulley 223c.

Further, the z-axis linear driving device 221 may include a ball screw block 227 combined to the ball screw shaft 224, and the movable frame 250 which the ball screw block 227 is installed in a central position of. The plurality (e.g., four) of guide blocks 226 may be combined to the guide bars 225 in a state where they are installed at the frame corner positions of the movable frame 250, respectively.

The movable frame 250 can maintain a horizontal state with respect to the bottom block 222 through the plurality of guide blocks 226. Further, the movement of the movable frame 250 may be guided in an extension direction of the guide bar 225 by the plurality of guide blocks 226.

Further, the z-axis linear driving device 221 may include a sensor bar 261 which extends toward the bottom block 222 from a side of the movable frame 250, and a displacement sensor 260 provided at a side surface of the bottom block 222 so as to sense change in a magnetic field by the sensor bar 261. In this regard, the sensor bar 261 may extend downward so as to be included in a sensing region of the displacement sensor 260.

Also, the displacement sensor 260 may be a potentiometer or hole sensor connected to the control unit 400. The displacement sensor 260 may measure displacement of the movable frame 250 to which the sensor bar 261 is mounted correspondingly to a change amount by which the magnetic field changes when the sensor bar 261 approaches or moves away from the sensing region of the displacement sensor 260, and may input the displacement measurement into the control unit 400.

The movement of the base 210 may be performed similarly to the movement of the movable frame 250.

The control unit 400 may precisely control the z-axis direction height of the base 210 connected to the movable frame 250 correspondingly to the displacement measurement through the displacement sensor 260.

Further, the z-axis linear driving device 221 may include a plurality of support bars 251 which are supported while being erected on the movable frame 250 with respect to positions which are not superimposed on the guide blocks 226. Both ends of the support bar 251 may be provided with fastening holes, respectively. The both ends of the support bar 251 may be combined between the movable frame 250 and the base 210 by means of the fastening hole and a bolt.

For example, there may be provided the four support bars 251 of the same height. Therefore, the plurality of support bars 251 can support the heater 240 and the base 210 horizontally with respect to the movable frame 250.

Further, each support bar 251 may be installed at the upper surface of the movable frame 250 corresponding to a position between the guide bars 225. That is, the support bar 251 and the guide bar 225 have a sequential disposition structure or zigzag disposition structure such that they are not superimposed on each other, and as a result, there is an advantage that the platform 200 may exhibit a stable supporting force and conveying force even with a compact device configuration.

Further, the end of the support bar 251 may be combined to the base 210 via a bolt in a state where it is in contact with the heater 240 for the platform 200 of the lower surface of the base 210.

The heater 240 may be combined to the lower surface of the base 210 in a bolt fastening method, an adhesive method or a double injection method.

The heater 240 may heat the base 210. For example, the heater 240 may be a pad type heating element or film type heating element having a planar area corresponding to the lower surface of the base 210. With this, uniform heat may be transferred to the entire base 210, and the hydrogel discharged on the film 20 may be uniformly heated. In the embodiment, the heater 240 is described by way of example as being a pad type or film type member, but the spirit of the invention is not limited to this. For example, the base 210 may be formed with a metal material which can transfer heat, and the heater may be a thermoelement connected to a side of the base 210.

The heater 240 may repeat the heating or non-heating of the base 210 according to a control signal (e.g., heater power application or cut-off) of the control unit 400. That is, the control unit 400 can control the movement of the nozzle modules 310, 350 and the operation of the pump 340, and maintain the temperature of the base 210 to a predetermined range by controlling the operation of the heater 240. As a result, the heat generated at the heater 240 can maintain to a predetermined range the temperature of the hydrogel on the film 20 through the film 20 on the base 210.

The heater 240 may be provided with a connection terminal 241 and a cable 242, so that it can be connected to the control unit 400. For example, in the connection terminal 241, there may be further installed a separate temperature sensor 243 which is connected to the control unit 400 via the cable 242 and measures temperature of the base 210 or temperature of the heater 240. That is, the control unit 400 can control the heater 240 based on a measurement which has been measured at the temperature sensor 243.

For example, the base 210 can be maintained to a predetermined temperature by the control unit 400 which receives feedback of a temperature measurement of the temperature sensor 243. Of course, an output temperature of the heater 240 required to maintain the base 210 to a predetermined temperature may be determined so as to be equal to or greater than the predetermined temperature.

Further, the z-axis linear driving device 221 may include the fixed frame 270 which is disposed between the movable frame 250 and the heater 240 for the platform 200 and which is combined to the end of the guide bar 225.

In this case, a bearing 271 at a central position of the fixed frame 270 may be combined to the end (e.g., upper end) of the ball screw shaft 224. Also, the opposite end (e.g., a lower end) of the ball screw shaft 224 is combined to the bearing 222a located at the bottom block 222 while being aligned with the shaft center of the bearing.

Further, at four sides of the fixed frame 270 with reference to the central position of the fixing frame 270, there may be provides recesses 272. The recess 272 may have a groove shape, hole shape or U-shaped cutaway shape, and play a role of allowing the support bar 251 to pass therethrough in a state where it does not contact the support bar 251.

By connecting by the plurality of guide bars 225 the fixed frame 270 and the bottom block 222 which are disposed spaced apart from each other along a vertical direction of the platform 200 and parallel to each other to form a frame type structure, the platform 200 can support the movable frame 250 and the base 210 without any no oscillation, which can maximize the degree of precision of the production of the skin care pack.

Hereinafter, the operation method of the platform 200 will be described.

The control unit 400 may control the driving motor 223 of the z-axis linear driving device 221 to move relatively to the above-described former 300.

According to the control of this control unit 400, the driving motor 223 may generate rotational force R corresponding to the forward rotation or reverse rotation. The rotational force R of the driving motor 223 is transmitted to the ball screw shaft 224 through the driving pulley 223a, the belt 223b and the driven pulley 223c. The rotational force R transmitted to the ball screw shaft 224 is converted to a vertical (e.g., z-axis direction) conveying force M through the ball screw block 227.

The conveying force M transmitted to the ball screw block 227 can move (e.g., ascend or descend) the movable frame 250, the support bar 251, the heater 240, and the base 210 so that the platform 200 can perform a relative movement with respect to the former 300.

This movement of the base 210 allows for the adjustment of the thickness of hydrogel or the thickness of a pattern part for a mask pack formed of hydrogel which can be discharged or layered on the film 20.

Particular, the plurality of guide blocks 226 are disposed with reference to a diagonal direction corresponding to the frame corner positions of the movable frame 250, and the plurality of support bars 251 are disposed with reference to an x-axis direction and a y-axis direction between the guide blocks 226.

Accordingly, the movable frame 250 can be ascended or descended in the z-axis direction without being shaken or eccentric, and the base 210 supported by the support bar 251 of the movable frame 250 can be also ascended or descended while being kept parallel to the movable frame 250.

Further, the heater 240 for the platform 200 can heat the base 240, and as a result can transfer heat to a lower surface of a mask pack which is formed on the film 20. At this time, the heat can be applied to hydrogel which has been discharged from the nozzle 311 of the nozzle modules 310, 350 and then layered on the film 20 in the form of a pattern part for the mask pack, and thus excessive hardening of hydrogel can be prevented. As a result, in the pattern part for a mask pack, a non-uniform portion is not formed, and thus a high quality mask pack can be formed.

Hereinafter, a control method of a device for producing a skin care pack using hydrogel as described above will be described.

The control unit 400 moves or stops the base 210 of the platform 200 in the housing 100 using the z-axis linear driving device 221, and moves the x-axis linear device 323 and the y-axis linear driving devices 321, 322 of the former 300, so that it can control a series of processes of forming a mask pack by discharging hydrogel, which is a raw material for producing a mask pack, toward the platform 200 through at least one nozzle module (310, 350) of the former 300. As this control process of the device for producing a skin care pack using hydrogel may be understood as being similar to that of a general 3D printer device.

For example, the control unit 400 may control the relative movement between the platform 200 on which a skin care pack is formed and the former 300 which discharges heated hydrogel. And, hydrogel may be discharged toward the platform 200 through at least one nozzle module 310, 350 which is provided to the former 300.

Further, the control unit 400 may control the temperature of the main block 330 or the temperature of hydrogel moving through the main block 330 within a temperature range corresponding to a heating condition of a skin care pack forming by activating the heater 332 installed in the main block 330.

Further, the control unit 400 may control the relative movement between the platform 200 and the former 300. In this procedure, the control unit 400 can activate the peristaltic pump, so that heated hydrogel can be discharged at the nozzle 311 of the nozzle module 310, 350. In other words, the control unit 400 can activate the pump 340 in a forward rotation, which is the peristaltic, so that hydrogel heated by the heater 332 can be discharged at the nozzle 311 of the nozzle module 310, 350.

Further, the control unit 400 may directly heat the base 210 of the platform 200 with the heater 240 of the platform 200 according to the predetermined condition before hydrogel is discharged or in a state where the z-axis linear driving device 221 waits for operation. That is, with the heater 240 provided to the platform 200, the temperature of the base 210 on which hydrogel is discharged may be maintained to a predetermined range.

Also, the control unit 400 may adjust height displacement of the base 210 of the platform 200 by activating the driving motor 223 correspondingly to the displacement of the nozzle module 310, 350.

Further, the control unit 400 may stop the heater 240 from heating when mask pack production operation of the nozzle module 310, 350 has been completed.

Further, the control unit 400 may cool down the motor of the peristaltic pump, that is, the pump motor 346 of the pump 340 by activating the cooling device 500 which is provided to a side of the main block 330, according to a predetermined condition. Further, the flow which has cooled down the pump motor 346 may be discharged to the work space 101 in which a skin care pack is formed. Further, after completing the pattern part of the skin care pack, the control unit 400 may make the relative movement of the platform 200 and the former 300, and return the former 300 to its initial position. Here, a step of controlling the relative movement by the control unit 400 may include a step of moving the base 210 in the z-axis direction.

Also, the control unit 400 may transmit a return control signal to the driving motor 223, so that the base 210 can be returned to an operation stand-by position.

According to the device for producing a skin care pack using hydrogel and the control method thereof according to an embodiment of the invention, although hydrogel is used as a raw material in the production of a user-customized skin care pack, the problem that hydrogel is leaked from the nozzle 311 can be prevented, and thus it is possible to produce a skin care pack smoothly.

Further, as the hydrogel of a stable heating condition can be discharged by heating the main block 330 itself, the syringe 312, the pump 340, and the nozzle 311 through the heater 332 of the main block 330, it is possible to produce a skin care pack rapidly and precisely in spite of using hydrogel.

Further, since the leakage of hydrogel is prevented and fixed amount control is possible by using a peristaltic pump as the pump 340, it is possible to obtain a high quality hydrogel skin care pack which has a uniform thickness, and whose finish treat is neat.

Further, since the control unit 400 receives the input of user-customized modelling CAD data and produces a skin care pack by discharging hydrogel based on them, it is possible to obtain a skin care pack using hydrogel which is optimized to physical body features of a user.

While until now the devices for producing a skin care pack using hydrogel according to examples of the invention have been described as concrete embodiments, these are just exemplary embodiments, and the present invention should be construed in a broadest scope based on the fundamental technical ideas disclosed herein, rather than being limited to them. By combining or replacing a part or parts of embodiments disclosed herein, the ordinary skilled in the art may carry out a pattern of a shape which is not explicitly described herein, and however, it should be noted that it shall not depart from the scope of the invention. Besides, the ordinary skilled in the art may easily change or modify embodiments disclosed herein based on the disclosure, and however, it is obvious that such change or modification also falls within the scope of the invention.

INDUSTRIAL APPLICABILITY

The invention can be used in the cosmetics industry.

The invention claimed is:

1. A device for producing a skin care pack using hydrogel, the device comprising:
   a housing which is provided with a door for selectively opening and closing a work space for forming a skin care pack and which maintains a forming temperature required for producing the skin care pack;
   a platform including a base supported on a floor plate of the work space of the housing and a heater for heating hydrogel discharged onto the base;
   a former including one or more nozzle modules which are provided to be movable in the work space, each nozzle module having a pump for receiving a heated hydrogel and then discharging the same onto the platform through a nozzle; and
   a control unit which controls the movement of the nozzle modules and the operation of the pumps, and maintains the temperature of the base to a predetermined range by controlling the operation of the heater.

2. The device according to claim 1, wherein the heater is a pad type or film type heating element which is installed on a lower part of the base.

3. The device according to claim 2, wherein the heater has a planar area corresponding to a lower surface of the base.

4. The device according to claim 1, wherein on the base, a film is seated to which hydrogel is discharged to form a skin care pack,
   the base is formed of a thermally conductive material, so that it can transfer heat through the film to a skin care pack which is formed, and
   the heater heats the base.

5. The device according to claim 1, wherein on the platform, there is provided a temperature sensor which measures temperature of the base or the heater, and
   the control unit controls the heater based on a value which has been measured by the temperature sensor.

6. The device according to claim 1, wherein the skin care pack is produced in one or more divided segments,
   one of the segments has a plurality of portions connected to each other, each portion being continuously formed, and
   when one of the portions is formed to be discontinuous with another portion, the one portion and the other portions are connected to each other after a predetermined period of time has elapsed.

7. The device according to claim 1, wherein the nozzle module further includes a cooling device which cools down a pump motor of the pump, and
   wherein the cooling device includes a cooling fan disposed on a side of the pump motor, cools down the pump motor with flow generated at the cooling fan, and discharges to the work space the flow which has absorbed heat from the pump motor.

8. The device according to claim 1, wherein the former moves the nozzle module in an x-axis and y-axis directions, and
   the platform includes a z-axis linear driving device which moves the base in a z-axis direction.

9. The device according to claim 8, wherein the z-axis linear driving device includes:
   a bottom block installed at a floor plate of the housing;
   a driving motor disposed at a side of the bottom block;
   a ball screw shaft to which a rotational force of the driving motor is transferred, and which is rotatably combined based on the bottom block;
   a plurality of guide bars which are dispersedly disposed at a plurality of points of the bottom block based on the ball screw shaft; and
   guide blocks which are slidably combined to the guide bars respectively.

10. The device according to claim 9, wherein the z-axis linear driving device includes:
   a ball screw block which is combined to the ball screw shaft, and which converts a rotational force of the ball screw shaft to a conveying force; and
   a movable frame which the ball screw block is installed at a central position thereof, and
   wherein the guide blocks are installed at frame corner positions of the movable frame respectively.

11. The device according to claim 10, wherein the z-axis linear driving device includes:
a plurality of support bars which are supported by the movable frame with reference to positions which are not superimposed on the guide blocks, each support bar is installed at the upper surface of the movable frame corresponding to a position between the guide bars, and wherein the base is combined to the end of the support bar so as to be supported by the support bar.

12. The device according to claim 11, wherein the z-axis linear driving device includes:
a fixed frame which is disposed between the movable frame and the heater, and which is combined to the end of the guide bar.

13. The device according to claim 9, wherein the bottom block includes:
a first sub-block at which the driving motor is installed;
a second sub-block which integrally extends from the first sub-block and which is provided with a disposition space of a driving force transmission mechanism; and
a third sub-block which are integrally formed on both sides of the second sub-block and which is provide with a groove.

14. The device according to claim 13, wherein the driving force transmission mechanism includes:
a driving pulley axially combined to a shaft of the driving motor;
a driven pulley axially combined to the ball screw shaft; and
a belt interconnecting the driving pulley and the driven pulley.

15. The device according to claim 10, wherein the z-axis linear driving device includes:
a sensor bar which extends toward the bottom block from a side of the movable frame; and
a displacement sensor provided at a side surface of the bottom block so as to sense change in a magnetic field by the sensor bar.

16. A control method of a device for producing a skin care pack using hydrogel which forms the skin care pack, in which a control unit controls a relative movement of a platform on which the skin care pack is formed and a former which discharges heated hydrogel, and hydrogel is discharged toward the platform through at least one nozzle module provided in the former, wherein the nozzle module includes a peristaltic pump, the control method comprising:
controlling a temperature of the main block of the nozzle module or a temperature of the hydrogel moving through the main block within a temperature range corresponding to a heating condition of a mask pack forming;
controlling a relative movement of the platform and the former;
discharging heated hydrogel at a nozzle of the nozzle module by activating the peristaltic pump;
maintaining a temperature of a base to which hydrogel is discharged to a predetermined range with a heater provided to the platform; and
returning the former to its initial position of operation by causing relative movement between the platform and the former after a pattern part of a skin care pack has been completed.

17. The control method according to claim 16, wherein the temperature of the base is lower than that of hydrogel which is discharged at the nozzle module.

18. The control method according to claim 16, further comprising:
cooling a motor of the peristaltic pump by activating a cooling device provided at a side of the main block,
wherein flow which has cooled down the motor of the peristaltic pump is discharged to a work space in which a skin care pack is formed.

19. The control method according to claim 16, wherein the platform includes a z-axis linear driving device, and
wherein the controlling of the relative movement includes:
moving the base in a z-axis direction.

* * * * *